(12) United States Patent
Sakamoto et al.

(10) Patent No.: US 11,572,537 B2
(45) Date of Patent: Feb. 7, 2023

(54) CELL HANDLING DEVICE

(71) Applicant: YAMAHA HATSUDOKI KABUSHIKI KAISHA, Iwata (JP)

(72) Inventors: Masaru Sakamoto, Shizuoka (JP); Saburo Ito, Shizuoka (JP); Takahiko Kumagai, Shizuoka (JP)

(73) Assignee: YAMAHA HATSUDOKI KABUSHIKI KAISHA, Iwata (JP)

( * ) Notice: Subject to any disclaimer, the term of this patent is extended or adjusted under 35 U.S.C. 154(b) by 449 days.

(21) Appl. No.: 16/603,050

(22) PCT Filed: Feb. 26, 2018

(86) PCT No.: PCT/JP2018/006966
§ 371 (c)(1),
(2) Date: Oct. 4, 2019

(87) PCT Pub. No.: WO2018/193718
PCT Pub. Date: Oct. 25, 2018

(65) Prior Publication Data
US 2020/0048598 A1    Feb. 13, 2020

(30) Foreign Application Priority Data

Apr. 20, 2017    (JP) .............................. JP2017-083908

(51) Int. Cl.
*C12M 1/26*    (2006.01)
*C12M 1/32*    (2006.01)
(Continued)

(52) U.S. Cl.
CPC ........... *C12M 33/04* (2013.01); *B01L 3/0237* (2013.01); *B01L 3/5085* (2013.01); *C12M 23/12* (2013.01);
(Continued)

(58) Field of Classification Search
CPC ...... C12M 33/04; C12M 33/06; C12M 23/50; C12M 23/12; C12M 41/48; B01L 3/0237;
(Continued)

(56) References Cited

U.S. PATENT DOCUMENTS 4,554,839 A  *  11/1985  Hewett .................. B01L 3/5085
422/561
2008/0273786 A1    11/2008  Komori et al.
(Continued)

FOREIGN PATENT DOCUMENTS

CN        101048492 A      10/2007
CN        101072881 A      11/2007
(Continued)

OTHER PUBLICATIONS

International Search Report issued in PCT/JP2018/006966; dated May 22, 2018.
(Continued)

*Primary Examiner* — Michael L Hobbs
(74) *Attorney, Agent, or Firm* — Studebaker & Brackett PC

(57) ABSTRACT

The cell handling device includes a container having a section to store cells; a cell detection unit for detecting a cell stored in the section; a head device for conducting picking of cells, and transfer and release of the picked cells; a control unit; and a determination unit for making a determination of a cell state including at least one of the number, properties, and arrangement of the cells based on a detection result of the cell detection unit. The control unit causes the head device to execute, according to a state determination result obtained by the determination unit, one operation selected from among operation of picking all the cells stored in the section, operation of picking a part of the cells stored in the section, operation of picking a new cell and releasing the cell
(Continued)

in the section, and operation of terminating processing of the section.

10 Claims, 17 Drawing Sheets

(51) Int. Cl.
*C12M 1/00* (2006.01)
*C12M 1/36* (2006.01)
*B01L 3/02* (2006.01)
*B01L 3/00* (2006.01)

(52) U.S. Cl.
CPC ............ *C12M 23/50* (2013.01); *C12M 41/48* (2013.01); *B01L 2200/0647* (2013.01)

(58) Field of Classification Search
CPC .................. B01L 3/5085; B01L 3/022; B01L 2200/0647; B01L 2200/143
See application file for complete search history.

(56) References Cited

U.S. PATENT DOCUMENTS

| | | | | |
|---|---|---|---|---|
| 2009/0117004 A1* | 5/2009 | Fritchie | .................. | B03C 1/284 422/63 |
| 2009/0232381 A1 | 9/2009 | Matsunaga et al. | | |
| 2011/0124037 A1* | 5/2011 | Backhaus | .............. | C12M 41/06 435/30 |
| 2014/0051114 A1 | 2/2014 | Ebi et al. | | |
| 2014/0120192 A1 | 5/2014 | Nakayama et al. | | |
| 2016/0304821 A1 | 10/2016 | Ito | | |
| 2017/0145362 A1 | 5/2017 | Ito | | |
| 2017/0145373 A1* | 5/2017 | Lianides | .............. | C12N 5/0601 |
| 2017/0159002 A1 | 6/2017 | Ito | | |
| 2018/0203028 A1 | 7/2018 | Ito | | |
| 2019/0055507 A1 | 2/2019 | Ito | | |

FOREIGN PATENT DOCUMENTS

| | | |
|---|---|---|
| CN | 106471113 A | 3/2017 |
| EP | 3 156 478 A1 | 4/2017 |
| JP | 2006333710 A | 12/2006 |
| JP | 20135751 A | 1/2013 |
| JP | 2014036618 A | 2/2014 |
| JP | 2014100109 A | 6/2014 |
| WO | 2015087371 A1 | 6/2015 |
| WO | 2016020992 A1 | 2/2016 |
| WO | 2017017990 A1 | 2/2017 |

OTHER PUBLICATIONS

The extended European search report issued by the European Patent Office dated Mar. 2, 2020, which corresponds to EP18788636.1-1101 and is related to U.S. Appl. No. 16/603,050.

An Office Action mailed by The State Intellectual Property Office of People's Republic of China dated Jun. 15, 2022, which corresponds to Chinese Patent Application No. 201880025175.4 and is related to U.S. Appl. No. 16/603,050 with English language translation.

* cited by examiner

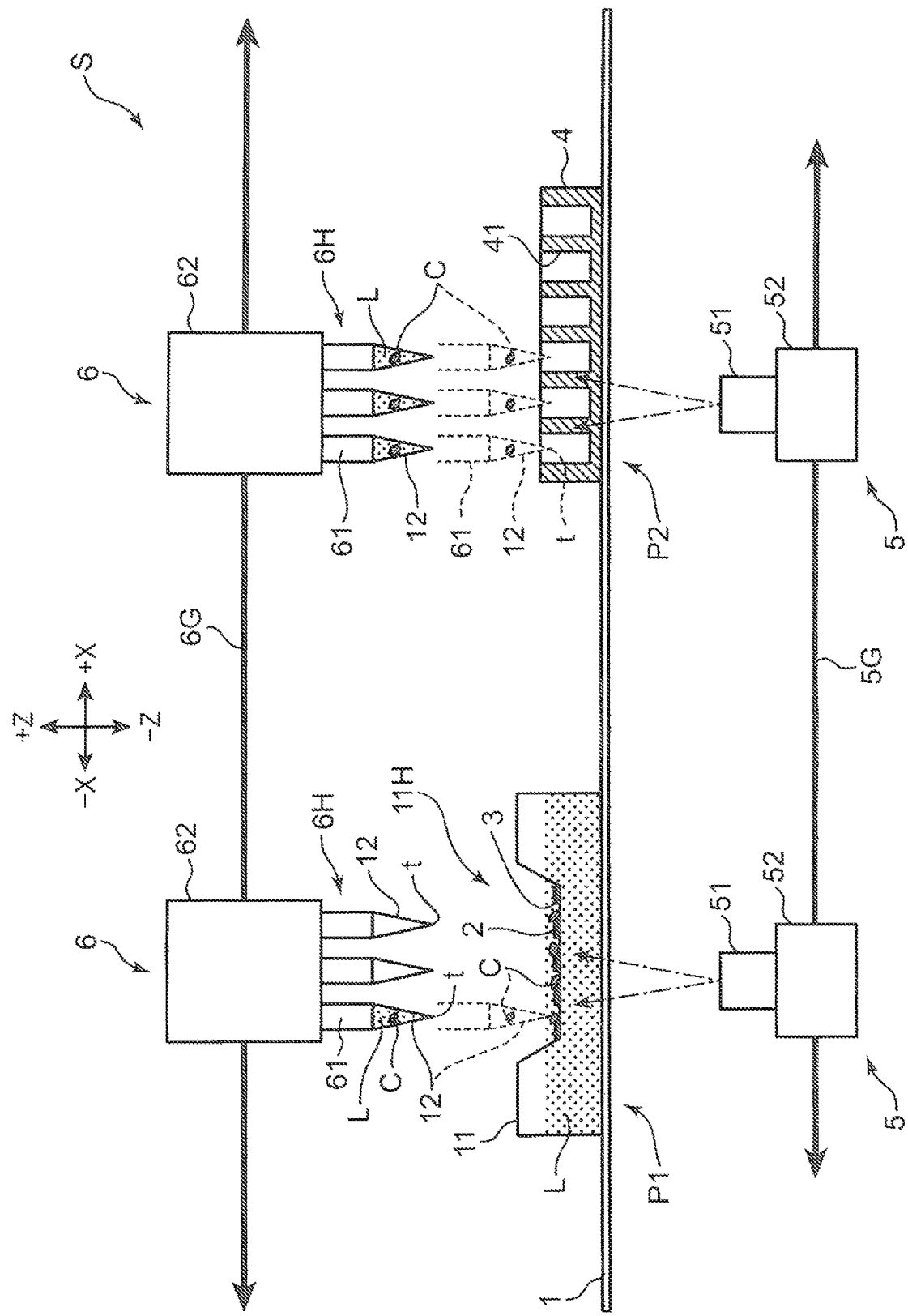

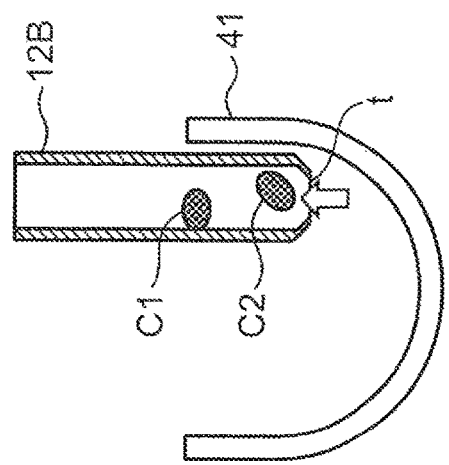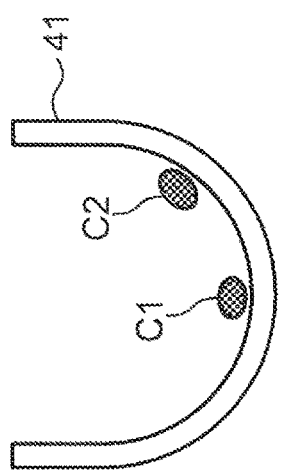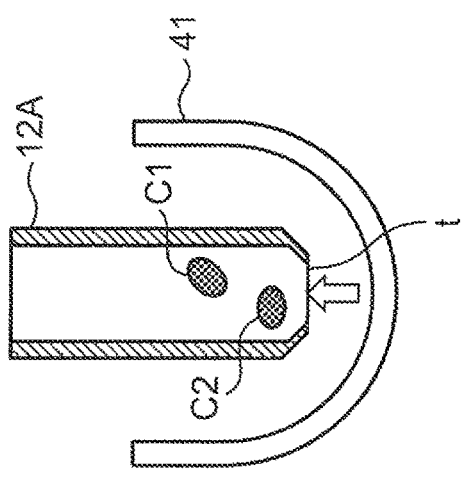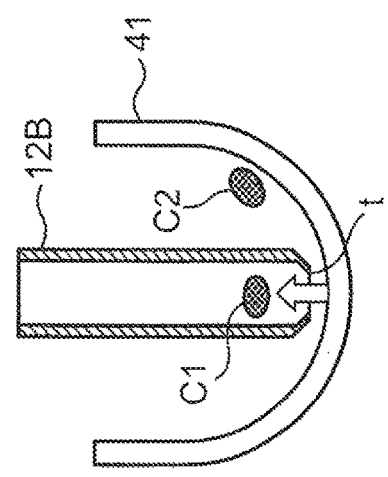

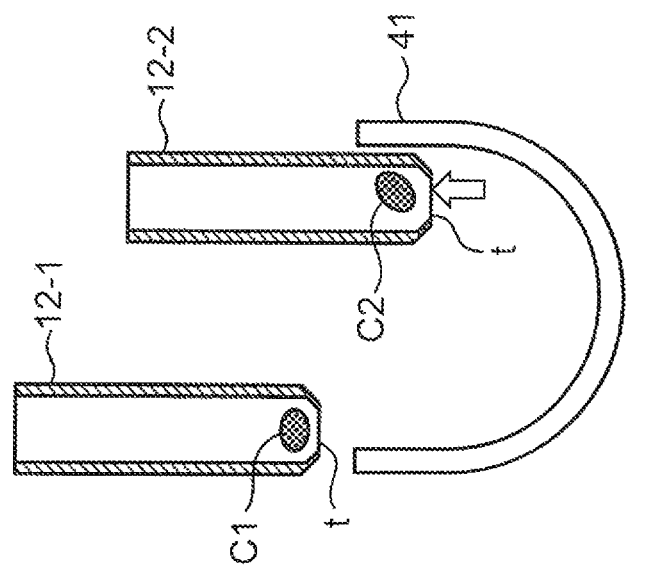
FIG. 8B
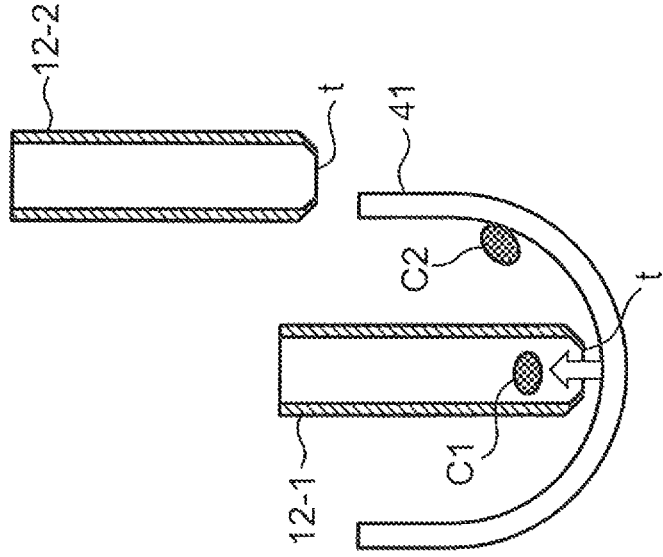
FIG. 8A
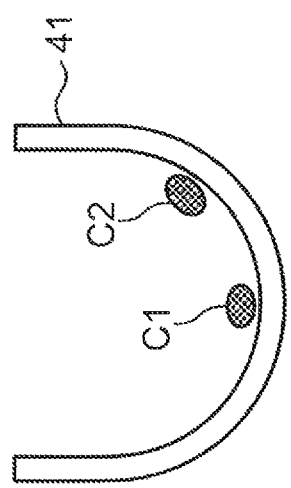

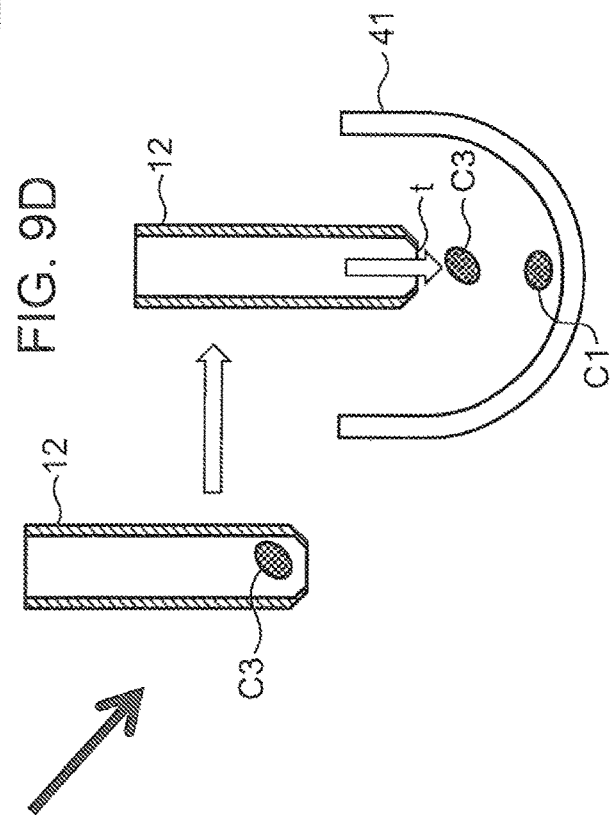

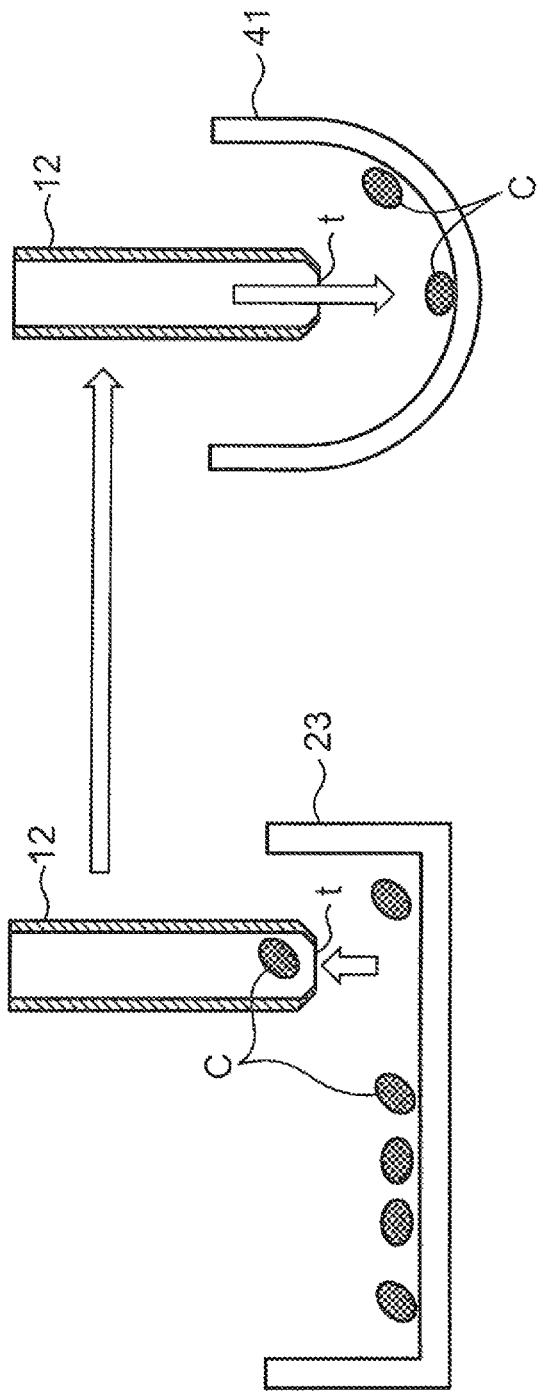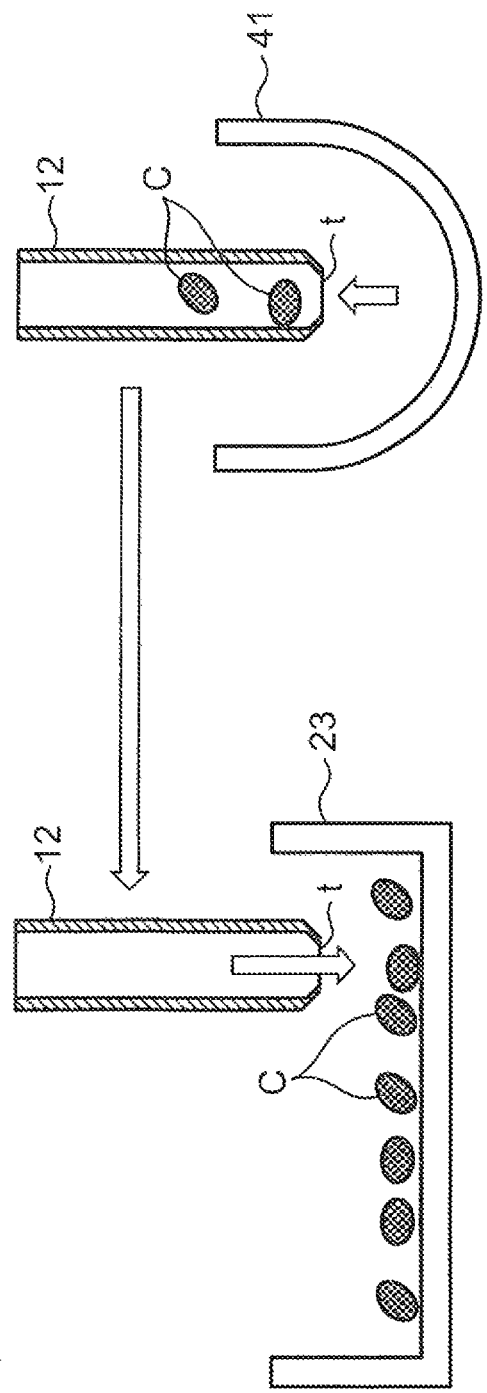

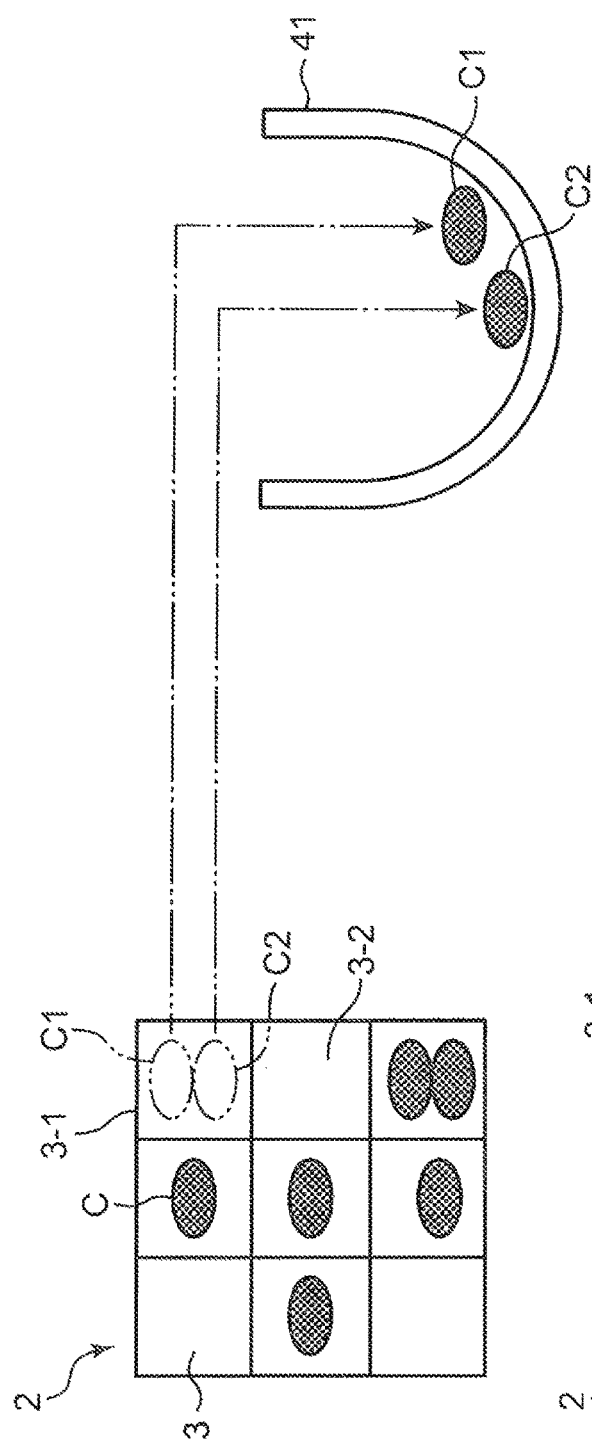
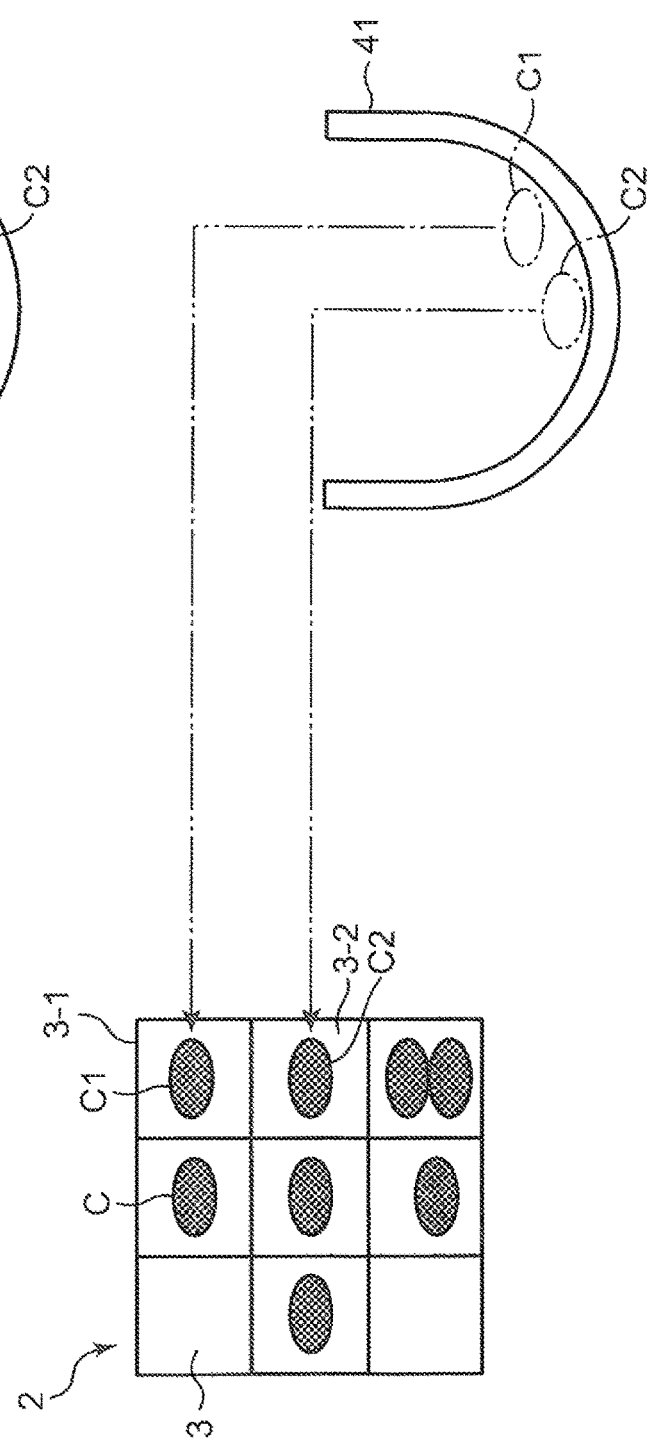
FIG. 13A
FIG. 13B

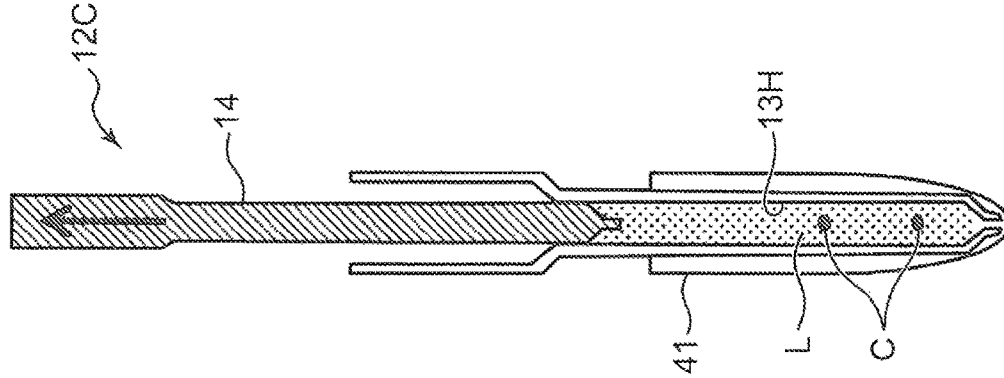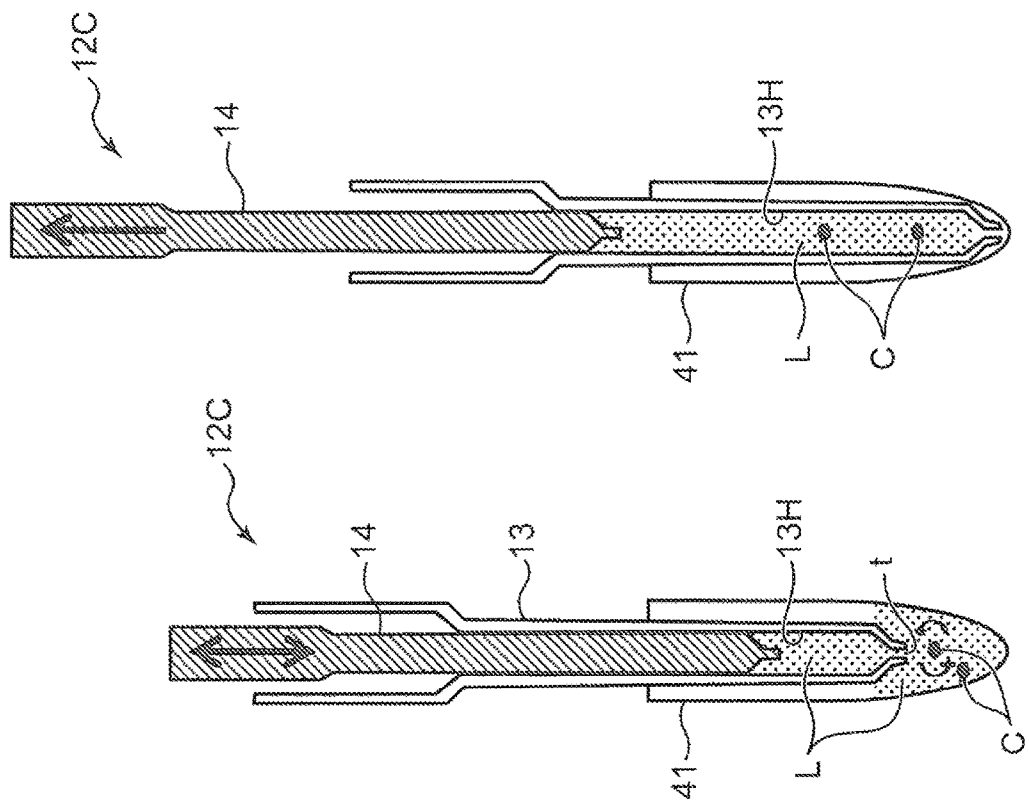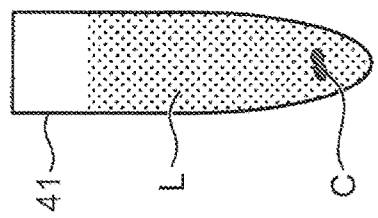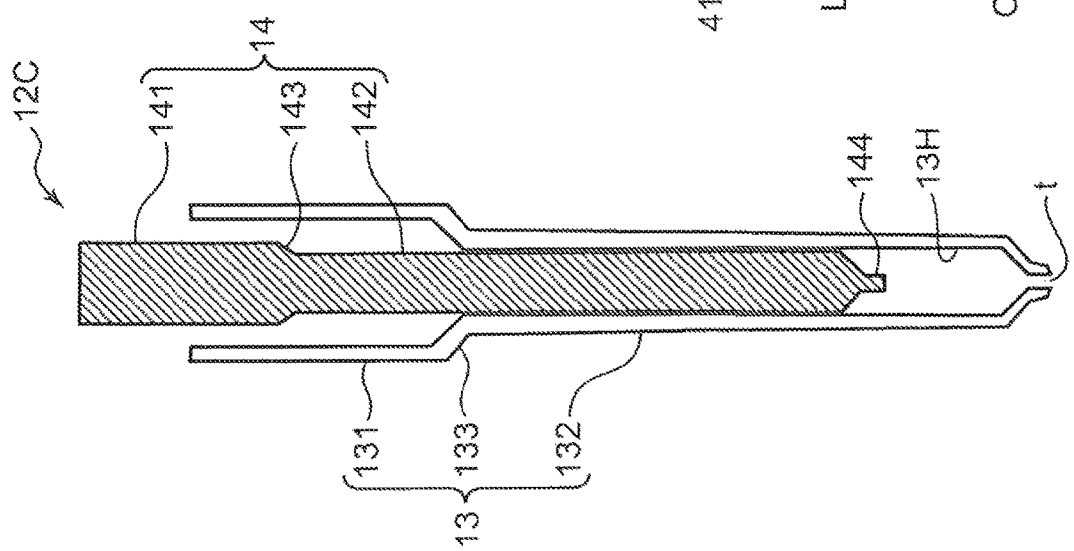

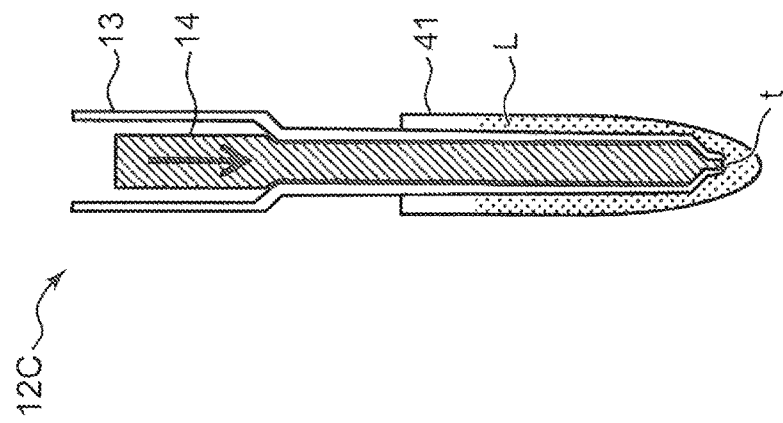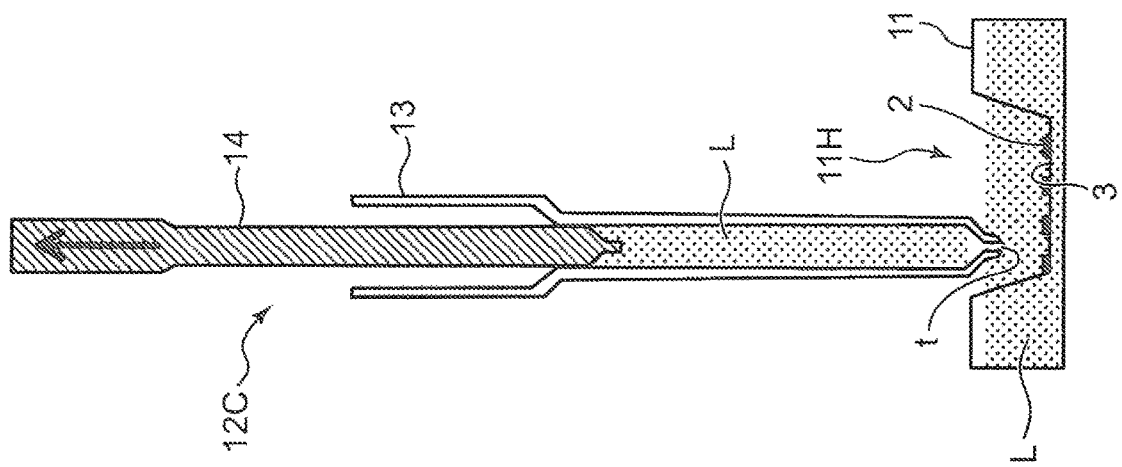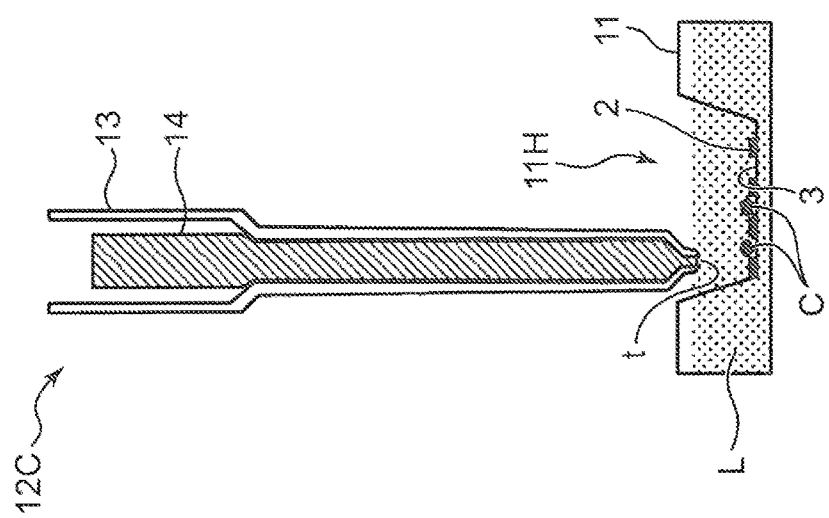

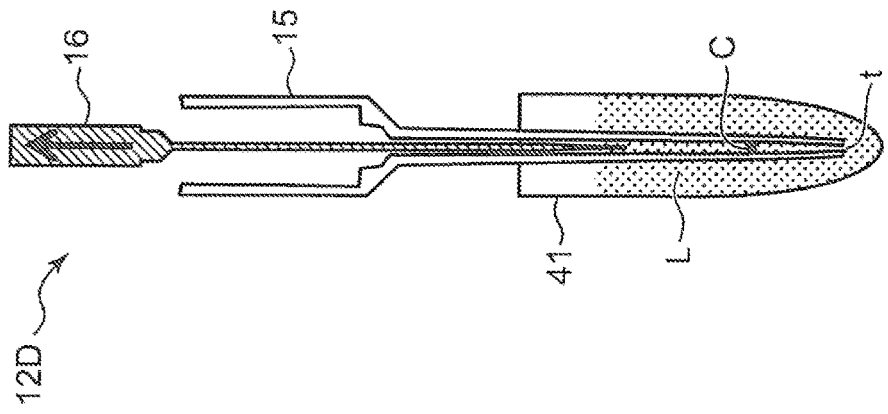
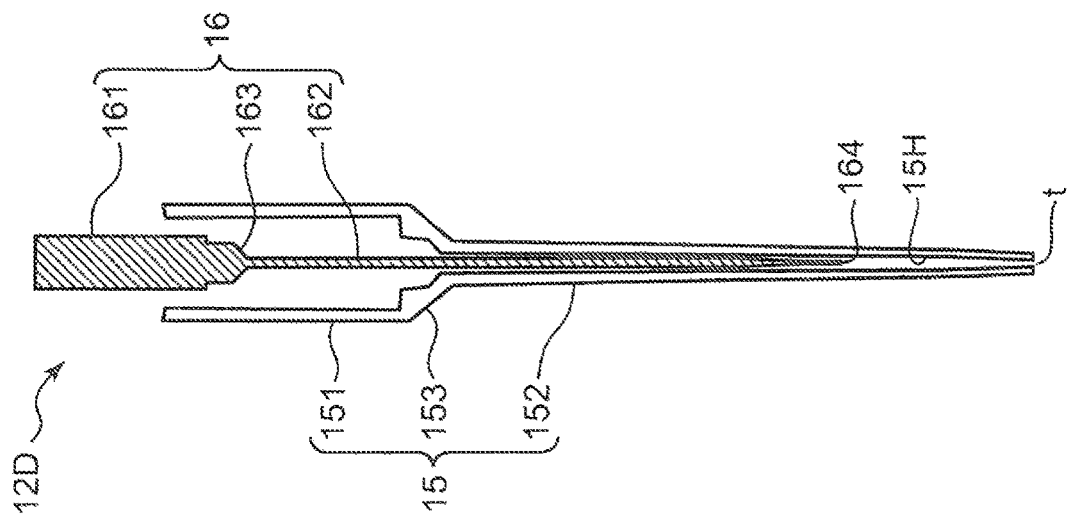

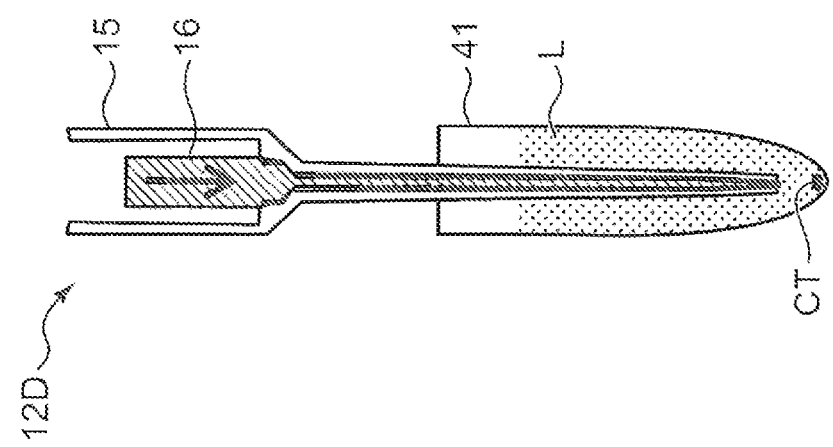
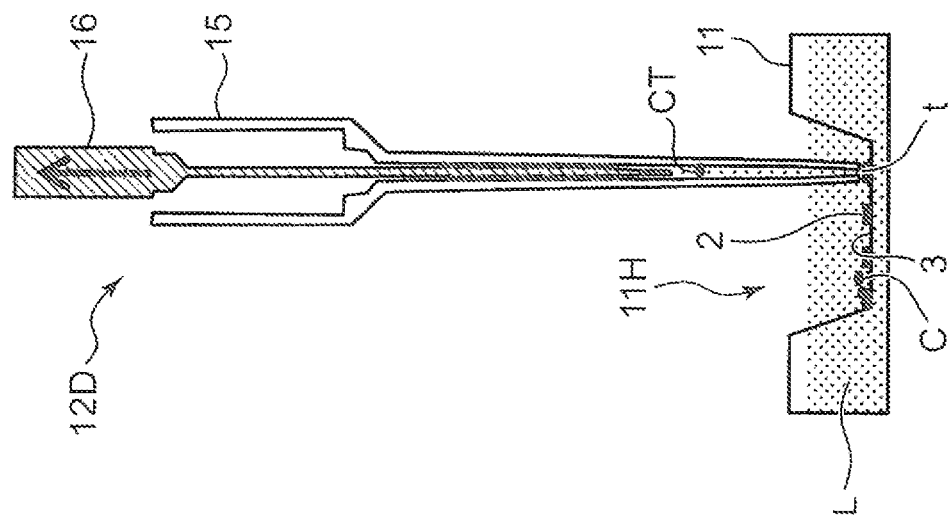
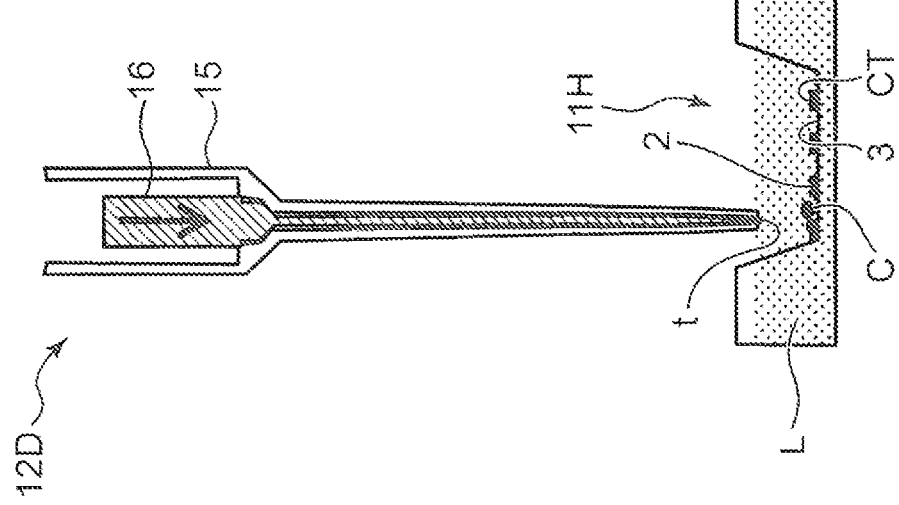

CELL HANDLING DEVICE

CROSS-REFERENCE TO RELATED APPLICATIONS

This application is a National Stage of International Patent Application No. PCT/JP2018/006966, filed Feb. 26, 2018, which claims benefit from JP 2017-083908, filed Apr. 20, 2017, the entire content of each are incorporated herein by reference.

BACKGROUND

Technical Field

The present disclosure relates to a cell handling device including a head device which conducts picking of cells, and transfer and release of the picked cells.

Background Art

For example, in applications for medical or biological research, there is a case where a single cell, or a cellular aggregate which is a result of three-dimensional agglomeration of cells, or a cell mass obtained by agglomerating and culturing a piece of a cell (hereinafter, simply referred to as a cell in the present specification) is stored in a well of a microplate having wells aligned in a matrix for the purpose of processing work such as observation, checking of efficacy of medicines, examination, or culture. A cell to be stored in the well is selected on a dish having a holding recess which can store a cell.

Specifically, a group of cells dispersed in a cell suspension is scattered on the dish by using a dispensation tip. The group of cells scattered here includes cells of various sizes and shapes. By capturing an image of the dish and executing image processing and the like, a cell suited for the processing work is selected from among these cells. The selected cell is picked from the dish by a tip capable of suctioning and discharging the cell and is also transferred to the microplate and discharged (released) to the well. For transferring such a cell from, for example, the dish to the microplate, there is used a cell handling device including a head device which conducts picking of cells and transfer and release of the picked cells as described, for example, in WO2015/087371.

For smooth proceeding of the subsequent processing work, it is desirable that a cell is stored in an intended state in the well to be a cell transfer destination. For example, in a case where a state of a cell is inappropriate, the state including properties of cells such as the number, size, shape, life and death, and good or bad of the cells stored in the well, and cell arrangement in the well, a trouble may occur in the processing work. However, there has not been proposed a cell handling device capable of modifying a state of a cell as intended in a container at a transfer destination.

SUMMARY

Accordingly, the present disclosure provides a cell handling device capable of bringing a container having a section for storing cells into a state where the cells are stored as intended.

A cell handling device according to one aspect of the present disclosure includes a container having a section capable of storing cells; a cell detection unit which detects a cell stored in the section; a head device which conducts picking of cells, and transfer and release of the picked cells; a control unit which controls operation of the head device; and a determination unit which makes a determination of a cell state including at least one of the number, properties and arrangement of the cells stored in the section based on a detection result of the cell detection unit. The control unit causes the head device to execute, according to a state determination result obtained by the determination unit, one operation selected from among operation of picking all the cells stored in the section, operation of picking a part of the cells stored in the section, operation of picking a new cell and releasing the cell in the section, and operation of terminating processing of the section.

BRIEF DESCRIPTION OF THE DRAWINGS

FIG. 1 is a view schematically showing a cell transfer device to which a cell handling device according to the present disclosure is applied;

FIGS. 7A to 7D are views showing one example of cell handling operation.

FIGS. 8A to 8C are views showing one example of the cell handling operation.

FIGS. 9A to 9E are views showing one example of the cell handling operation.

FIGS. 12A and 12B are views showing one example of the cell handling operation.

FIGS. 13A and 13B are views showing one example of the cell handling operation.

FIGS. 14A to 14D are views showing one example of the cell handling operation.

FIGS. 15A to 15C are views showing one example of the cell handling operation.

FIGS. 16A to 16C are views showing one example of the cell handling operation; and FIGS. 17A to 17C are views showing one example of the cell handling operation.

DETAILED DESCRIPTION

Figure 2A:
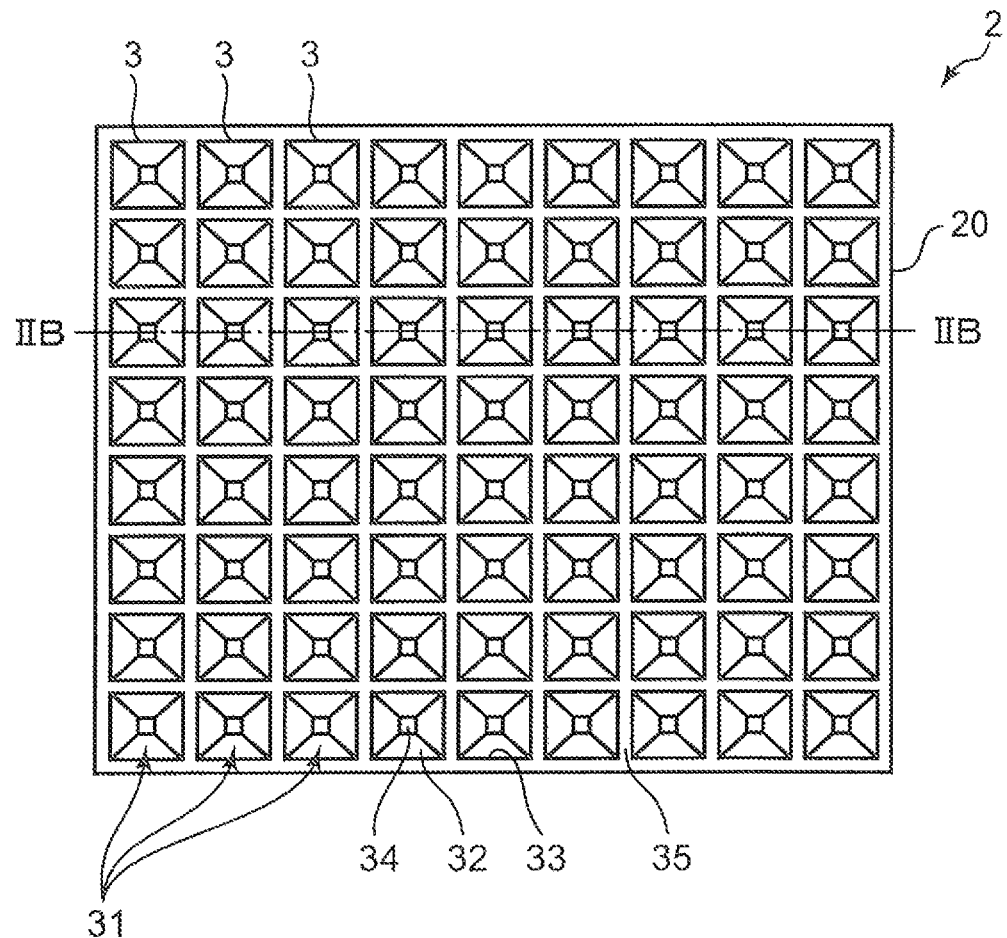
FIG. 2A is a top view of a dish provided in a selection container for use in the cell transfer device.

In the following, embodiments of the present disclosure will be described in detail with reference to the drawings. In a cell handling device according to the present disclosure, a tissue-derived cell, a cell mass, a cellular aggregate (spheroid) or the like is used as a handling target. For example, a tissue-derived cellular aggregate is formed by agglomerating several to several hundred thousands of cells. Therefore, a cellular aggregate varies in size. Although a cellular aggregate formed by a living cell is generally spherical, when a part of a cell constituting the cellular aggregate deteriorates or becomes a dead cell, the cellular aggregate may have a distorted shape or have uneven density in some cases. In a test for a biology-related technique or in a medical field, a cell handling device (cell transfer device) is used which picks a usable cellular aggregate by a tip from among a plurality of cellular aggregates having various shapes which is carried by a dish on a selection stage, and transfers the picked cellular aggregate to a microplate and releases the cellular aggregate thereat. On the microplate, various processing is executed for the cellular aggregate, such as observation, checking of efficacy of medicines, examination, and culture. In the following description, in view of including such a cellular aggregate as described above, the cellular aggregate will be expressed simply as a cell C.

[Overall Configuration of Cell Transfer Device]

FIG. 1 is a view schematically showing an overall configuration of a cell transfer device S to which a cell handling device according to the present disclosure is applied. Here, the cell transfer device S which transfers the cell C between two containers is illustrated. X and Z directions shown in FIG. 1 represent, for example, a right-left direction and an up-down direction, in which +X represents right, −X left, +Z up, and −Z down. A Y direction represents a direction orthogonal to both the X direction and the Z direction, and corresponds to, for example, a front-rear direction.

The cell transfer device S includes a light transmissive base 1 having a level mounting surface (an upper surface), a camera unit 5 (a part of a cell detection unit/an imaging device) arranged below the base 1, and a head unit 6 (a head device) arranged above the base 1. At a first mounting position P1 of the base 1, a selection container 11 provided with a dish 2 (a cell holder) is mounted and at a second mounting position P2, a microplate 4 (a container) is mounted. The head unit 6 includes a head group 6H having a plurality of heads 61 movable in the Z direction, to which heads 61, tips 12 (a part of the head device) for suctioning and discharging the cell C is attached. The camera unit 5 and the head unit 6 are movable in the X direction and the Y direction. The dish 2 and the microplate 4 are mounted on the upper surface of the base 1 within a movable range of the head unit 6.

Roughly explained, the cell transfer device S is a device which individually suctions the cell C by each of the plurality of tips 12 from the dish 2 of the selection container 11 which holds numerous cells C, and transfers the cells C to the microplate 4, and also simultaneously or individually discharges the cells C from the plurality of tips 12 to the microplate 4 (a well 41). Each unit of the cell transfer device S will be described in the following.

The base 1 is a rectangular flat plate having predetermined rigidity and a part or all of the base 1 is formed with a light transmissive material. The base 1 is preferably a glass plate. Forming the base 1 with a light transmissive material such as a glass plate allows the camera unit 5 arranged below the base 1 to capture the image of the selection container 11 (the dish 2) and the microplate 4 arranged on the upper surface of the base 1 through the base 1.

The selection container 11 is a container as a transfer source of the cell C, and accumulates a culture medium L and holds the cell selection dish 2 being immersed in the culture medium L. The dish 2 is a plate which holds the cell C and has, on its upper surface, holding recesses 3 (holding portions) capable of individually storing and holding the cells C. The culture medium L is not particularly limited as long as it does not deteriorate properties of the cell C, and can be appropriately selected according to a kind of the cell C.

The selection container 11 is provided, on its upper surface side, with a rectangular upper opening 11H. The upper opening 11H is an opening for inserting the cell C and picking the selected cell C. The dish 2 is arranged below the upper opening 11H. The selection container 11 and the dish 2 for use are made of a light transmissive resin material or glass. This is for enabling the camera unit 5 arranged below the selection container 11 to observe the cell C carried on the dish 2.

The plurality of cells C being dispersed in a cell culture solution are injected to the selection container 11 from the dispensation tip (not shown). The dispensation tip suctions, from the container which accumulates a cell culture solution containing a large number of the cells C, the cell culture solution together with the cells C and holds the solution and the cells in the dispensation tip. Thereafter, the dispensation tip is moved to a position above the selection container 11 to access the upper surface of the dish 2 through the upper opening 11H. Then, with a distal end opening of the dispensation tip immersed in the culture medium L of the selection container 11, the cell C held in the dispensation tip is discharged on the dish 2 together with the cell culture solution.

Figure 2B:
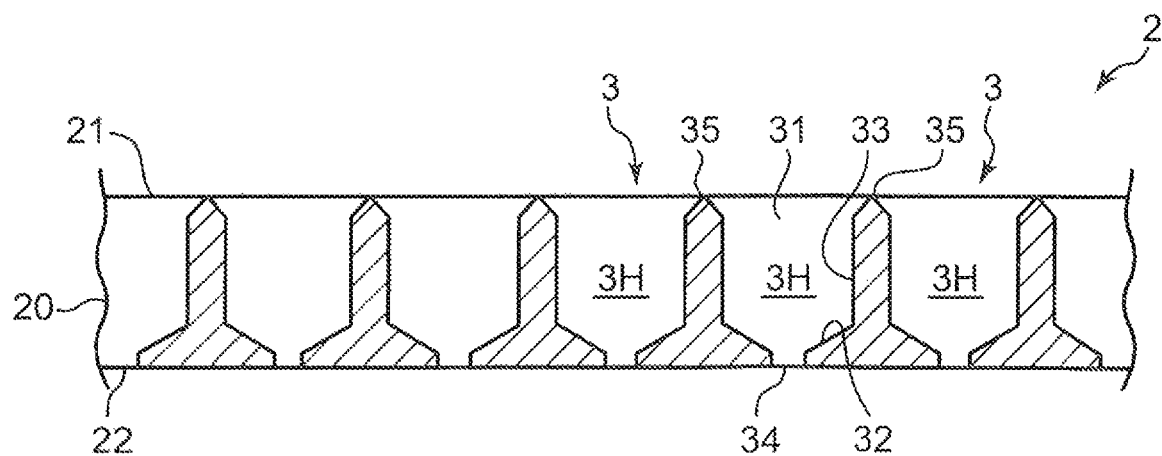
FIG. 2B is a sectional view taken along line IIB-IIB in FIG. 2A.

Detailed structure of the dish 2 will be described. FIG. 2A is a top view of the dish 2, and FIG. 2B is a sectional view take along line IIB-IIB in FIG. 2A. The dish 2 is provided with a dish main body 20 and a plurality of holding recesses 3 formed in the dish main body 20. The dish main body 20 is made of a flat plate-shaped member having a predetermined thickness and has an upper surface 21 and a lower surface 22. The holding recess 3 has a reception opening (opening portion 31) for the cell C on the side of the upper surface 21. The dish 2 is immersed in the culture medium L in the selection container 11. Specifically, while the upper surface 21 of the dish main body 20 is immersed in the culture medium L in the selection container 11, the lower surface 22 is held in the selection container 11 in a state of being spaced from a bottom plate of the selection container 11 (see FIG. 1).

Each of the holding recesses 3 includes the opening portion 31, a bottom portion 32, a tubular wall surface 33, a hole portion 34 and a boundary portion 35. In the present embodiment, there is shown an example where the holding recesses 3 which is square in a top view is aligned in a matrix. The opening portion 31 is a square opening provided in the upper surface 21 and has a size which allows a distal end opening portion t of the tip 12 for selection to enter. The bottom portion 32 is positioned within the dish main body 20 and near the lower surface 22. The bottom portion 32 is an inclined surface gradually slanting toward the center (the center of the square). The tubular wall surface 33 is a wall surface extending vertically downward from the opening portion 31 toward the bottom portion 32. The hole portion 34 is a through-hole vertically penetrating between the center of the bottom portion 32 and the lower surface 22. The boundary portion 35 is a portion positioned in the upper surface 21 and corresponding to an opening edge of each holding recess 3 and is a ridgeline that partitions the holding recesses 3.

The bottom portion 32 and the tubular wall surface 33 of each holding recess 3 partition a storage space 3H which stores the cell C. The storage space 3H is in general intended to store one cell C. The hole portion 34 is provided for causing small cells and impurities of a size other than a desired size to escape from the storage space 3H. Accordingly, the hole portion 34 has a size selected to prevent the cell C of a desired size from passing through but allow small cells and impurities of a size other than the desired size to pass through. In this manner, the cell C to be selected is trapped in the holding recess 3, while impurities and the like drop from the hole portion 34 to the bottom plate of the selection container 11.

Returning to FIG. 1, the microplate 4 is a container which becomes a transfer destination of the cell C and has a plurality of wells 41 (sections capable of storing cells) to which the cells C are discharged. The well 41 is a bottomed hole which is opened in an upper surface of the microplate 4. In one well 41, a necessary number of the cells C are stored together with the culture medium L. The microplate 4 used here is also made of a light transmissive resin material or glass. This is for enabling the cell C carried in the well 41 to be observed by the camera unit 5 arranged below the microplate 4.

Figure 3A:
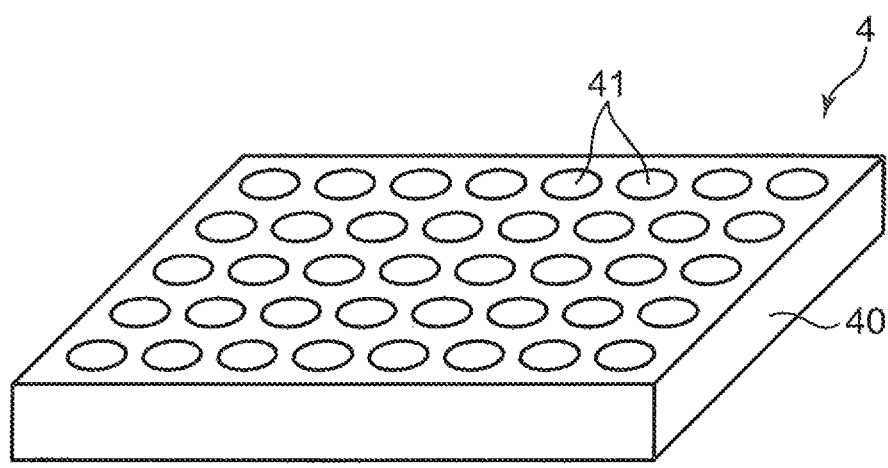
FIG. 3A is a perspective view of a microplate for use in the cell transfer device and FIG. 3B is a sectional view of the microplate.

FIG. 3A is a perspective view showing one example of the microplate 4. The microplate 4 includes a plate main body 40 and the plurality of wells 41 aligned in the plate main body 40 in a matrix. Since the distal end opening portion t of the tip 12 enters the well 41 during discharge of the cell C, each well 41 has an opening diameter which allows the tip 12 to enter with a margin.

Figure 3B:
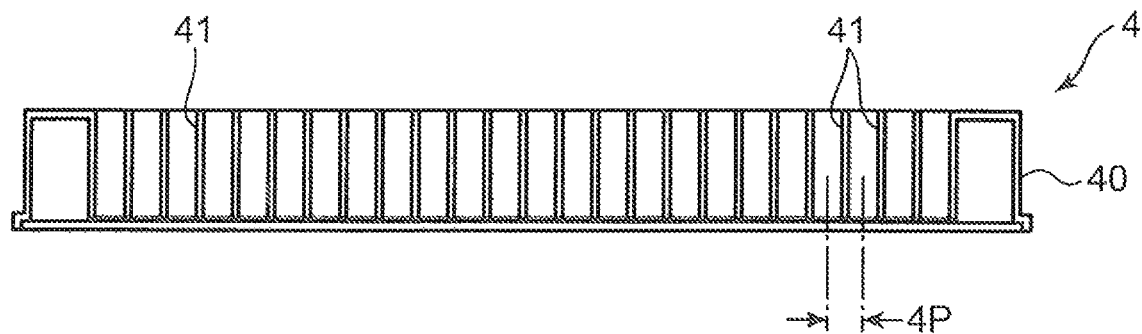

Commercially available microplates have a standard size. A standard microplate has a predetermined length-to-width size (length 85.48 mm×width 126 mm) and has a predetermined number of wells. A general number of wells is 24×16 (384 wells), the wells being aligned at a predetermined pitch in a matrix. FIG. 3B is a sectional view of the microplate 4 with 384 wells. As shown in the figure, 24 wells 41 are aligned at an equal well pitch 4P in a longitudinal direction of the microplate 4 (16 in a shorter side direction).

The camera unit 5, which captures an image of the cell C held in the holding recess 3 of the dish 2 or the well 41 (section) of the microplate 4 from their lower sides to obtain an image of the cell C, is provided with a lens unit 51 and a camera main body 52. In the present embodiment, the camera unit 5 functions as a part of the cell detection unit which detects the cell C stored in the well 41.

The lens unit 51 is an objective lens for use in an optical microscope and includes a lens group which forms an optical image of a predetermined magnification, and a lens barrel which houses a lens group. The camera main body 52 is provided with an imaging element such as a CCD image sensor. The lens unit 51 forms an optical image of an imaging target on a light receiving surface of the imaging element. The camera unit 5 is movable along a guide rail 5G extending in the right-left direction in parallel with the base 1, under the base 1 and in the X direction. Although not illustrated in FIG. 1, the camera unit 5 is movable also in the Y direction. The lens unit 51 is movable in the Z direction for focusing operation.

The head unit 6 is provided for transferring the cell C from the dish 2 to the microplate 4 and includes the head group 6H including the plurality of heads 61, and a head main body 62 in which the head group 6H is installed. The tip 12 which conducts suctioning and discharging of the cell C is attached to a distal end of each head 61. The head main body 62 holds the head 61 so as to be raised and lowered in +Z and −Z directions and is movable along a guide rail 6G in +X and X directions. Although not illustrated in FIG. 1, the head main body 62 is movable also in the Y direction. In the present embodiment, the head unit 6 functions as the head device which conducts picking (suctioning by the tip 12) of the cell C and transfer and release (discharging by the tip 12) of the picked cell C.

The head 61 is formed with a hollow rod having a negative pressure generation mechanism attached. In a hollow portion of the head 61, for example, a piston mechanism is mounted, so that operation of the piston mechanism applies suction force and discharge force to the distal end opening portion t of the tip 12. The head main body 62 is internally provided with a power unit of the piston mechanism, and a raising and lowering mechanism which causes the head 61 to move in the up-down direction and its power unit (a head drive unit 64 to be described later).

Figure 4:
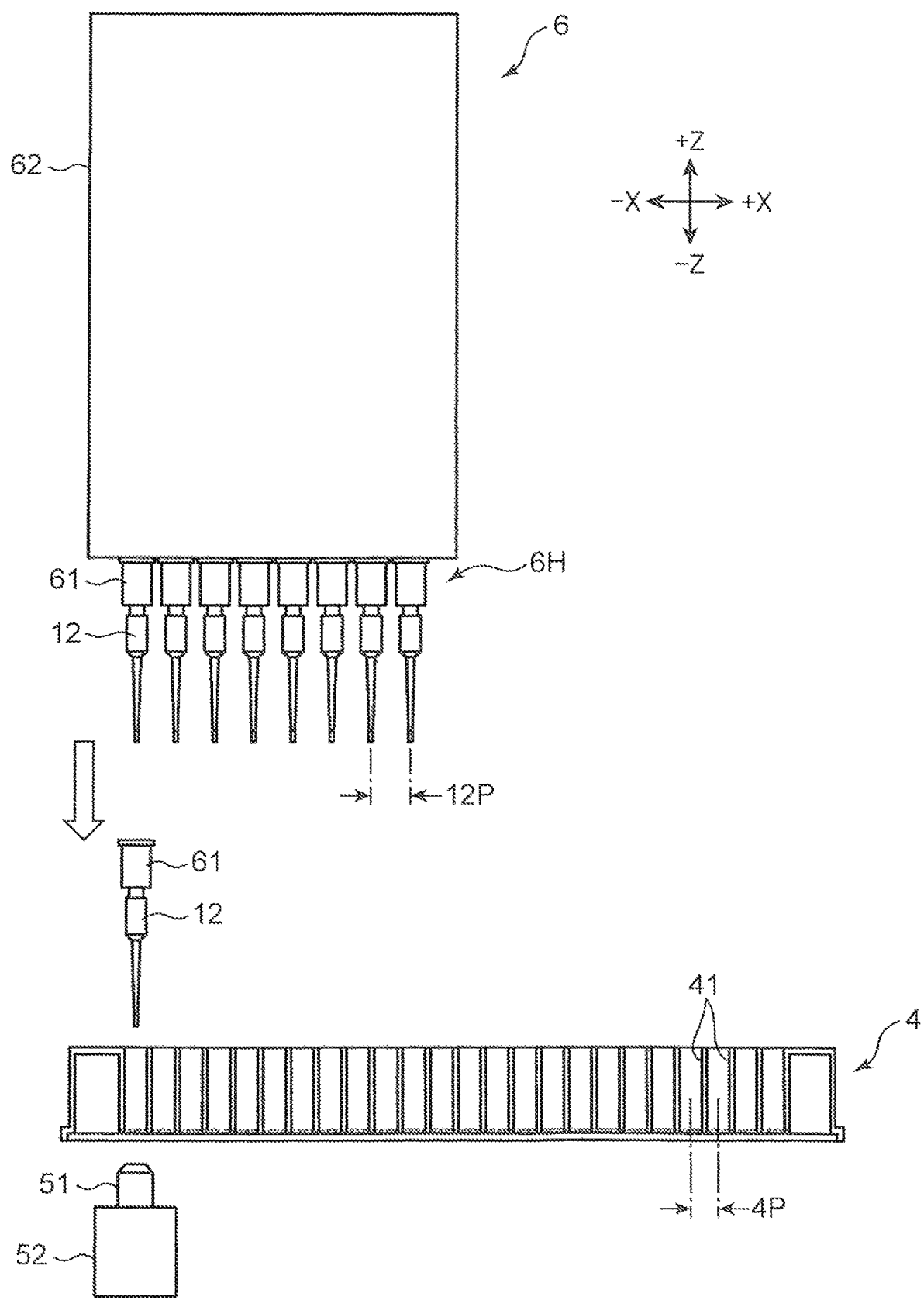
FIG. 4 is a view showing a relation among a head unit, the microplate and a camera unit in the cell transfer device.

FIG. 4 is a view showing a specific example of the head unit 6 and shows a relation between the microplate 4 and the camera unit 5. In the head unit 6, the head group 6H is exposed below from a lower end side (the −Z side) of the head main body 62. FIG. 4 illustrates the head group 6H including eight heads 61 linearly aligned in the X direction. FIG. 4 also illustrates a state where one head 61 lowers and the tip 12 attached to the head 61 accesses one well 41 of the microplate 4 for picking or releasing the cell C. Prior to the picking or releasing, the well 41 is imaged by the camera unit 5 to check the number, properties and arrangement of the cells C transferred from the microplate 4 and stored in the well 41. Thereafter, the tip 12 conducts picking (suction) of a target cell C or release (discharge) of a new cell.

The plurality of tips 12 attached to the plurality of heads 61, respectively, are aligned in the X direction at a predetermined tip alignment pitch 12P. The tip alignment pitch 12P is n-times of the well pitch 4P (n is an integer of 1 or more) of the wells 41 in the microplate 4. For example, in the case of the microplate 4 having 384 wells, since the well pitch 4P is 4.5 mm as described above, the tip alignment pitch 12P is set to be 4.5 mm×2=9.0 mm. Selecting the well pitch 4P and the tip alignment pitch 12P in this manner allows the plurality of tips 12 to simultaneously access the plurality of wells 41 and to simultaneously discharge the cells C.

[Electrical Configuration of Cell Transfer Device]

Figure 5:
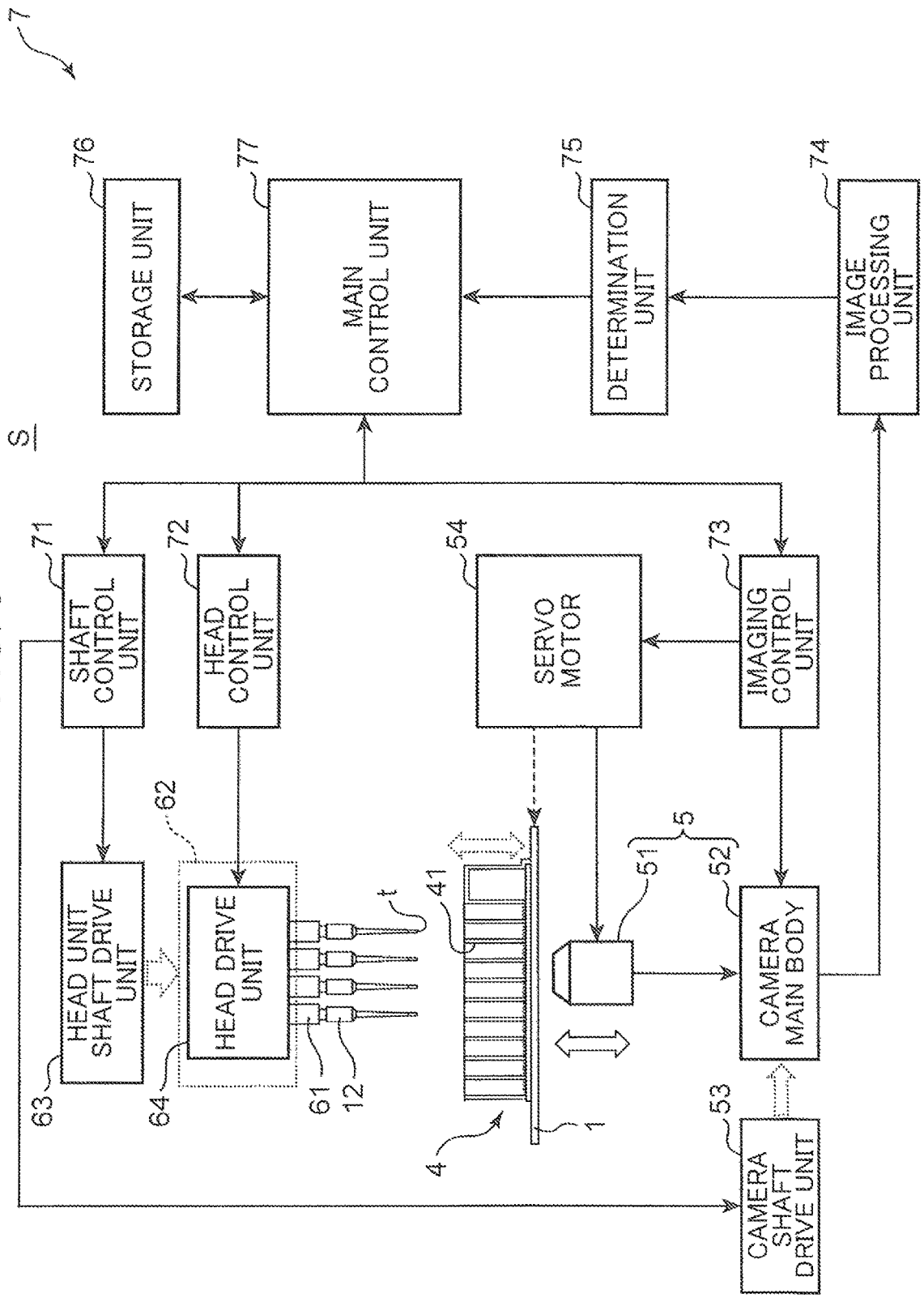
FIG. 5 is a block diagram showing an electrical configuration of the cell transfer device.

FIG. 5 is a block diagram showing an electrical configuration of the cell transfer device S. The cell transfer device S includes a control unit 7 which controls movement of the head unit 6, raising and lowering of the head 61, suctioning and discharging operations of the cell C, moving and imaging operations of the camera unit 5, and the like. The cell transfer device S also includes a camera shaft drive unit 53 as a mechanism which causes the camera unit 5 to move horizontally, a servo motor 54 as a drive source which causes the lens unit 51 to move up and down, a head unit shaft drive unit 63 as a mechanism which causes the head unit 6 to move horizontally, and the head drive unit 64 as a mechanism which raises and lowers the head 61 and as a mechanism which causes the head to conduct suctioning and discharging operations.

The camera shaft drive unit 53 includes a drive motor which causes the camera unit 5 to move horizontally along the guide rail 5G. In a preferable mode, a ball thread is laid along the guide rail 5G, the camera unit 5 is attached to a nut member screwed with the ball thread, and the drive motor causes forward rotation or reverse rotation of the ball thread, thereby moving the camera unit 5 to a target position.

Forward rotation or reverse rotation of the servo motor 54 causes the lens unit 51 to move with a predetermined resolution in the up-down direction via a power transmission mechanism (not shown). This movement allows a focal position of the lens unit 51 to be set to the cell C stored in the well 41. As indicated by a dotted line in FIG. 5, the microplate 4 itself or a stage (the base 1) on which the microplate 4 is mounted may be moved up and down by the servo motor 54 instead of moving the lens unit 51.

The head unit shaft drive unit 63 includes a drive motor which causes the head unit 6 (the head main body 62) to move along the guide rail 6G. In a preferable mode, with a ball thread and a nut member provided, the drive motor causes the ball thread to rotate forward or rotate reversely. In a case of moving the head main body 62 in the two directions of X and Y, a first ball thread (the X direction) along the guide rail 6G and a second ball thread (the Y direction) mounted on a moving plate attached to a first nut member screwed with the first ball thread are used. In this case, the head main body 62 is attached to a second nut member screwed with the second ball thread (the same applies to the camera shaft drive unit 53).

The head drive unit 64 is a power unit for the raising and lowering mechanism and a power unit (e.g. motor) for driving the piston mechanism and is incorporated in the head main body 62. The raising and lowering mechanism causes the head 61 to move up and down between a lowered position at which the head 61 protrudes downward from the head main body 62 and a raised position at which a most part of the head 61 is housed in the head main body 62. The power unit of the piston mechanism causes generation of suction force and discharge force at the distal end opening portion t of the tip 12 by raising and lowering a piston member arranged in the head 61.

The control unit 7 is configured with a microcomputer or the like, and functions to include the shaft control unit 71, a head control unit 72, an imaging control unit 73, an image processing unit 74 (a part of the cell detection unit), a determination unit 75, a storage unit 76, and a main control unit 77 (a control unit) as a result of execution of a predetermined program.

The shaft control unit 71 controls operation of the head unit shaft drive unit 63. Specifically, the shaft control unit 71 causes the head unit 6 to move to a predetermined target position in a horizontal direction by controlling the head unit shaft drive unit 63. Movement of the head 61 (the tip 12) between the selection container 11 and the microplate 4, positioning of the head 61 vertically above the holding recess 3 of the dish 2, and positioning of the head 61 vertically above the well 41 of the microplate 4 as a discharge target, and the like are realized by control of the head unit shaft drive unit 63 by the shaft control unit 71.

The head control unit 72 controls the head drive unit 64. The head control unit 72 causes the head 61 as a control target to be raised and lowered toward a predetermined target position by controlling the power unit for the raising and lowering mechanism of the head drive unit 64. The head control unit 72 also causes suction force or discharge force to be generated at the distal end opening portion t of the tip 12 at predetermined timing by controlling the power unit of the piston mechanism for the head 61 as a control target.

The imaging control unit 73 controls the camera shaft drive unit 53 to control operation of moving the camera unit 5 along the guide rail 5G. The imaging control unit 73 also controls imaging operation (amount of exposure, shutter timing, etc.) of the dish 2 or the microplate 4 by the camera unit 5. Further, the imaging control unit 73 applies a control pulse to the servo motor 54 to move the lens unit 51 in the up-down direction at a predetermined pitch (e.g. a pitch of several tens μm) for focusing operation.

The image processing unit 74 subjects image data obtained by the camera main body 52 to image processing such as pattern recognition processing involving edge detection processing or feature amount extraction. The image processing unit 74 executes processing of recognizing, on an image, presence (the number) of the cells C on the dish 2 (the holding recess 3), processing of recognizing distribution (arrangement) of the cells C, processing of recognizing properties of the cell C such as size, shape, color tone, and the like based on an image of the dish 2 to which the cells C have been dispensed. Similarly, the image processing unit 74 executes processing of recognizing the number, arrangement, and properties of the cells C stored in the well 41 based on an image of the well 41 to which the cells C have been transferred.

The determination unit 75 determines a state of the cell C based on a detection result of the cell C made by the camera unit 5 and the image processing unit 74. Specifically, the determination unit 75 determines a state of the cell C, including the number of the cells C present in one holding recess 3 or well 41 and arrangement of the cells C, and properties of the cell C such as size, shape, and color tone based on a recognition processing result of the cell C obtained by the image processing unit 74 with respect to the image data obtained by the camera unit 5.

To be specific with respect to the well 41, determination is made whether the number of the cells C is in short or in excess with respect to a reference number of the cells C to be stored in one well 41. It is also determined, based on arrangement of the cells C, whether or not the cells C are arranged at a predetermined distance from each other in the well 41, or with which position of the well 41, the cell C contacts (whether or not picking is easy), and the like.

It is further determined, based on properties of the cell C, whether or not the cell C is appropriate as a target of processing such as examination to be conducted later. At this time, the determination unit 75 determines whether or not the cell C as a determination target satisfies a determination criterion which is set in advance with respect to the properties. For example, in a case of a cell C whose size is too large or too small, determination of "No" is made. For a cell C with an extremely distorted shape, a dead cell, and a cell C having a color tone considered to be an unhealthy cell, determination of "No" is made.

The storage unit 76 stores various kinds of set values, data, programs, and the like in the cell transfer device S. The storage unit 76 additionally stores data related to the determination criterion of the cell C. For example, there are stored reference data related to properties such as size range, shape and color tone of the cell C determined by the determination unit 75 to be "good", and a distance between cells as a determination criterion for selecting either simultaneous suction or individual suction of the cell C.

The main control unit 77 conducts centralized control of operation of the camera unit 5 and the head unit 6 (the head device). The main control unit 77 controls the camera unit 5 and the head unit 6 through the shaft control unit 71, the head control unit 72, and the imaging control unit 73 so as to conduct imaging of the dish 2 where the cells C are scattered, selection of a cell C (good cell C) as a transfer target, and picking of a selected cell C at the first mounting position P1 (FIG. 1) where the selection container 11 is mounted. The main control unit 77 controls the camera unit 5 and the head unit 6 so as to conduct release of the picked cell C to the well 41, imaging of the well 41, and modification processing of forming a state where the cell C is stored in each well 41 as intended at the second mounting position P2 where the microplate 4 is mounted.

[Overall Operation of Cell Transfer Device]

Next, description will be made of overall operation of the cell transfer device S, i.e., cell transfer operation with reference to FIG. 1 and FIG. 5. First, operation of dispensing the cell C to the selection container 11 is executed. The plurality of cells C being dispersed in a cell culture solution are injected into the selection container 11 from the dispensation tip (not shown). In other words, the cells C are scattered on the dish 2.

Next, selecting operation of the cell C is executed. The shaft control unit 71 controls the camera shaft drive unit 53 to cause the camera unit 5 to move below the selection container 11 along the guide rail 5G. Then, the imaging control unit 73 controls the camera unit 5 to capture an image of the cell C carried on the dish 2. The image processing unit 74 subjects the obtained image data to predetermined image processing. Thereafter, determination is made of selecting a cell C (good cell C) as a transfer target by the determination unit 75. The selected cell C is handled as a picking target by the tip 12 to obtain its coordinate position.

Subsequently, cell transfer operation is executed. The shaft control unit 71 controls the head unit shaft drive unit 63 to move the head unit 6 to a position above the selection container 11. Then, the head control unit 72 controls the head drive unit 64 to lower the head 61, so that the distal end opening portion t of the tip 12 accesses the upper surface of the dish 2 through the upper opening 11H. At this time, XYZ coordinate information indicative of a position of the cell C as a transfer target is given to the shaft control unit 71 and the head control unit 72, so that the tip 12 accesses the holding recess 3 where the cell C is carried.

Thereafter, the head drive unit 64 causes the head 61 to generate suction force. As a result, a target cell C is suctioned (picking of the cell C) from the dish 2 (the holding recess 3) into the tip 12 together with the culture medium L. Then, the head 61 is raised and the head unit 6 is moved to a position above the microplate 4. When the head unit 6 arrives to the position above the microplate 4, the head 61 is again lowered until the distal end opening portion t of the tip 12 enters the well 41 of the microplate 4. Then, the head drive unit 64 causes the head 61 to generate discharge force, so that the cell C in the tip 12 is discharged to the well 41 together with the culture medium L. A discharge status of the cell C to the well 41 is checked by imaging of the microplate 4 (the well 41) by the camera unit 5.

Thereafter, a storage state of the cell C in the well 41 is recognized based on the image obtained by the imaging. Then, modification operation is executed for modifying a state such that a cell is stored in each well 41 as intended. There might occur a case where the cell C is not stored in each well 41 as intended even through the cell has been subjected to a cell selection step in advance by the selection operation on the dish 2 side. Reasons for the occurrence include a failure of suction of the cell C from the dish 2, unintended mixing of cells or impurities, insufficient discharge to the well 41, damage of the cell C during transfer, and the like. The modification operation is, for example, to bring about a state where a predetermined number of cells satisfying a predetermined determination criterion are stored in a predetermined well 41.

[Specific Example of Modification Operation]

The main control unit 77 causes the head unit 6 to execute predetermined modification operation with respect to each well 41 to which the cell C has been transferred according to a state determination result obtained by the determination unit 75. Specifically, the main control unit 77 causes the head unit 6 to execute one operation selected from the following operations 1 to 4 with respect to one well 41 as a target.

Operation 1: Operation of picking (suctioning) all the cells C stored in the well 41.

Operation 2: Operation of picking a part of the cells C stored in the well 41.

Operation 3: Operation of picking a new cell C to release (discharge) the cell to the well 41.

Operation 4: Operation of terminating processing of the well 41.

Operation 1 is picking operation executed in a case where, for example, all the cells C transferred to the target well 41 do not satisfy a predetermined determination criterion, to be specific, where all the cells C are defective. Operation 2 is picking operation executed, in a case where the plurality of cells C have been transferred to the target well 41, for removing an unnecessary cell C, or for extracting a necessary cell C and transferring the cell to another well 41 or another container. Operation 3 is operation executed, in a case where a required number of cells C are not stored in the target well 41, for adding, to the target well 41, the cell C picked from another well 41 (the cell C picked in Operation 2) or the cell C acquired from another place. Operation 4 is selected when it is confirmed that the cells C are stored in the target well 41 as intended. Operation 4 is, so to speak, operation of ignoring the target well 41 by the head unit 6, which involves no substantial operation in practice. In other words, the main control unit 77 causes the head unit 6 to execute one of Operations 1 to 3, or determines not to cause the head unit 6 to execute processing for one target well 41.

Figure 6:
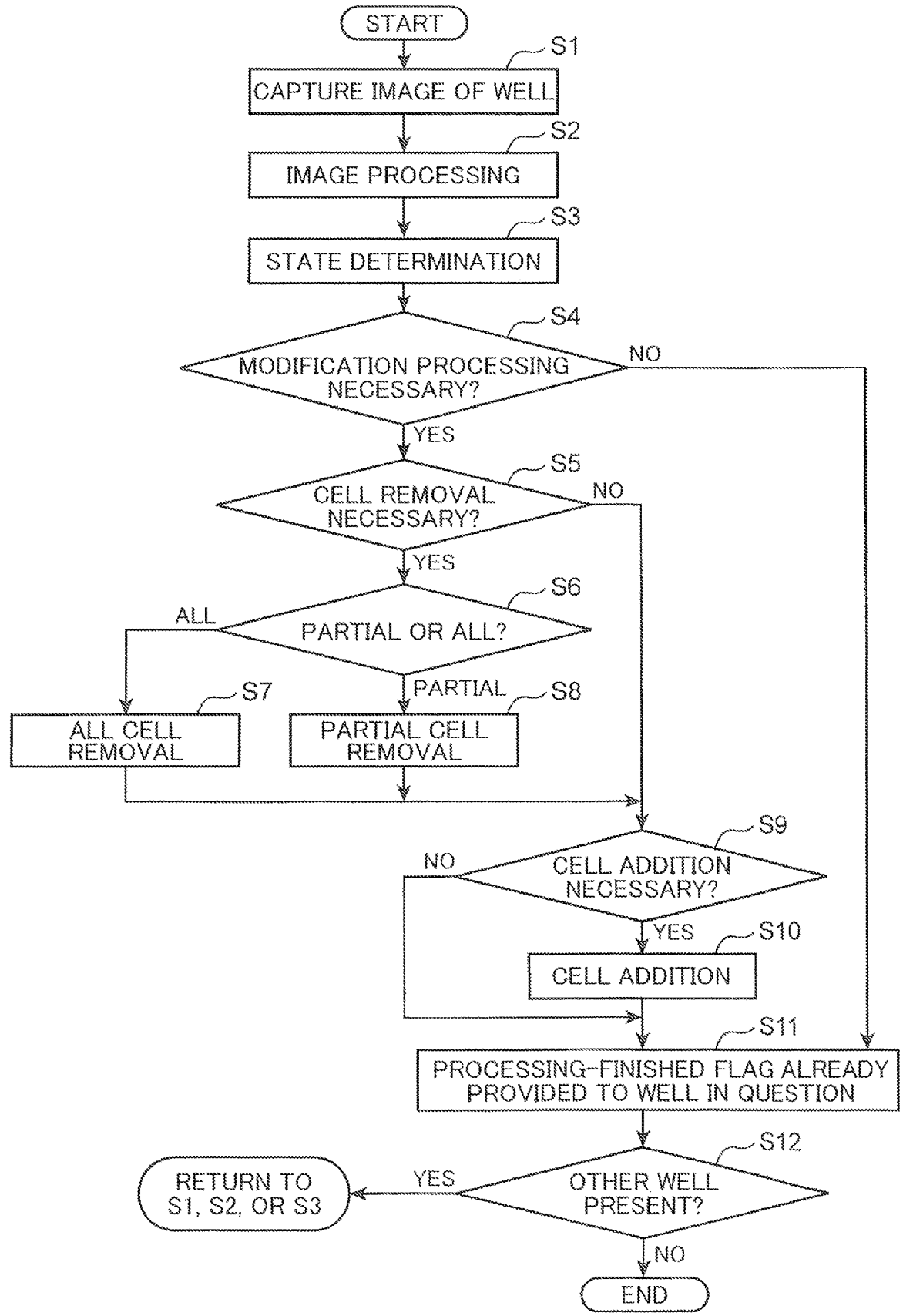
FIG. 6 is a flow chart showing one example of work selection processing for a head device by a main control unit.

FIG. 6 is a flow chart showing one example of operation selecting processing for the head unit 6 by the main control unit 77. When transferring of the cell C from the dish 2 to the microplate 4 is finished, the main control unit 77 causes the camera unit 5 to capture an image of the well 41 in which the cell C is stored via the imaging control unit 73 (Step 51). As described above, the image processing unit 74 subjects the obtained image data to the image processing to recognize the cell C (Step S2), and subsequently, the determination unit 75 makes determination as to a state of the cell C (Step S3). Steps S1 and S2 may be executed in advance with respect to all the wells 41 provided in the microplate 4 and data thereof may be temporarily stored in the storage unit 76. Alternatively, Steps S1 to S3 and the subsequent steps may be executed for each well 41.

Subsequently, with respect to the target well 41, the main control unit 77 determines whether or not modification processing such as removal and addition of the cell C is required based on the state determination result obtained by the determination unit 75 (Step S4). In a case where the cells C are stored in the target well 41 as intended, the main control unit 77 determines that the modification processing is unnecessary (NO in Step S4), and a processing-finished flag is provided in association with an identification sign of the target well 41 (Step S11). The processing corresponds to selection of the above "Operation 4".

On the other hand, in a case where the modification processing is determined to be necessary (YES in Step S4), the main control unit 77 determines whether or not it is necessary to remove the cells C from the target well 41 (Step S5). In a case where a more necessary number of the cells C is stored in the target well 41 or in a case where a defective cell C is stored, determination is made that cell removal is necessary (YES in Step S5). In this case, the main control unit 77 determines whether removal of only a part of the cells C is required or removal of all the cells is required (Step S6). Then, in a case where removal of all the cells C is required, all cell removal operation is selected corresponding to the above "Operation 1" (Step S7). On the other hand, in a case where removal of only a part of the cells C is required, partial cell removal operation is selected corresponding to the above "Operation 2" (Step S8).

After the determination in Step S7 or Step S8, or in a case of NO in Step S5, the main control unit 77 determines whether or not addition of the cell C to the target well 41 is necessary (Step S9). In a case where addition of the cells C is required because the cells C is short in number from the beginning or because removal of a part or all of the cells C causes shortage of the number of the cells C (YES in Step S9), cell addition operation corresponding to the above "Operation 3" is selected (Step S10). For the cell addition operation, the tip 12 which has conducted removal in Steps S7 and S8 may be used or another tip 12 may be used which has picked and held a good cell C in another well 41. In a case where cell addition is not required (NO in Step S9), Step S10 is skipped.

Thereafter, a processing-finished flag is provided so as to be associated with the identification sign of the target well 41 (Step S11). Then, it is checked whether or not the well 41 which requires the modification processing remains (Step S12), and in a case where such a well 41 remains (YES in Step S12), the processing returns to any of Step S1, S2 or S3, and the main control unit 77 executes the same processing with respect to the subsequent well 41. In a case where the well 41 does not remain (NO in Step S12), the processing ends.

[Example of Cell Handling]

In the following, specific examples of various kinds of cell handling corresponding to the above Operations 1 to 3 will be described with reference to FIG. 7 to FIG. 17. In these drawings, one or two wells 41 are schematically shown. Although the well 41 having a hemispherical bottom surface is illustrated here, the bottom surface may be a plane or a tapered face. Although the cells C are dispersed and held in the culture medium L (liquid) within the well 41, illustration of the culture medium L is omitted in FIG. 7 to FIG. 13.

Example 1

FIGS. 7A to 7D are views showing Example 1 of cell handling. Example 1 shows a specific example of all cell removal in the above Operation 1 (Step S7). As illustrated in FIG. 7A, it is assumed that two cells C1 and C2 are stored in one well 41 as a modification target. Both of the cells C1 and C2 are assumed to be defective cells which are determined not to satisfy a predetermined determination criterion by the determination unit 75 and assumed to be cells that should be removed. The cell C1 is positioned near the center of the bottom surface of the well 41 and the cell C2 is positioned near an edge of the hemispherical bottom surface.

In this case, two cells C1 and C2 may be suctioned at once by one suction operation by the tip 12 (one suction), or each suction operation may be conducted with respect to the cells C1 and C2 to allow the tip 12 to sequentially suction the cells C one by one (individual suction). FIG. 7B shows an example of the former one suction. Here, a large diameter tip 12A is used which is large in an opening diameter of the distal end opening portion t and in a tip internal diameter. With the large diameter tip 12A, suction force is likely to be generated near the distal end opening portion t in a relatively wide range, and even the cells C1 and C2 spaced apart from each other can be simultaneously suctioned. In this case, the main control unit 77 lowers the head 61 to allow the distal end opening portion t of the large diameter tip 12A to enter the well 41 and generate suction force. In this manner, the two cells C1 and C2 can be held in the large diameter tip 12A together with the culture medium.

FIGS. 7C and 7D show an example of the latter individual suction. Here, a small diameter tip 12B is used which is small in the opening diameter of the distal end opening portion t and in the tip internal diameter. With such a small diameter tip 12B, it is difficult to simultaneously suction the cells C1 and C2 spaced apart from each other. Accordingly, first, as shown in FIG. 7C, the main control unit 77 causes the distal end opening portion t of the small diameter tip 12B to be aligned with the cell C1 to suction the cell C1. Next, as shown in FIG. 7D, the head main body 62 is minutely moved to align the distal end opening portion t with the cell C2 to suction the cell C2. In this manner, two times of suction operation enable two cells C1 and C2 to be held in one small diameter tip 12B. In a case where the cells C1 and C2 are positioned close to each other, even the small diameter tip 12B may be allowed to simultaneously suction these cells.

According to Example 1, a cell C not satisfying a determination criterion is removed from the well 41 to bring the well 41 into a so-called reset state. Accordingly, by reinserting a new cell C which satisfies the determination criterion to the well 41, it is possible to modify the state to be a state where the cells C are stored in the well 41 as intended.

Example 2

FIGS. 8A to 8C are views showing Example 2 of cell handling. Example 2 is a modification of the above Example 1, which shows an example of using the plurality of tips 12 attached to the different heads 61 as picking tips in the operation of individually suctioning a plurality of cells C1 and C2 (operation of FIGS. 7C and 7D).

As shown in FIG. 8A, it is assumed that two cells C1 and C2 to be picked are stored in the target well 41. For picking, a first tip 12-1 attached to one head and a second tip 12-2 (another head device) attached to another head 61 are used. First, as shown in FIG. 8B, the distal end opening portion t of the first tip 12-1 is aligned with the cell C1 to suction the cell C1. Next, as shown in FIG. 8C, the head main body 62 is minutely moved to align the distal end opening portion t of the second tip 12-2 with the cell C2 to suction the cell C2. Thus, each suction operation by each of the first tip 12-1 and the second tip 12-2 enables the two cells C1 and C2 to be held by each tip.

Thus, in a case where a plurality of cells C to be picked is present in the well 41, it is preferable to set the main control unit 77 to select whether to pick all the cells C to be removed by one tip 12 (the example in FIG. 7) or to share picking of the cells C to be removed by the plurality of tips 12 (the example in FIG. 8). This diversifies picking and release patterns of the cells C to enable improvement of work efficiency. For example, in a case where both of the cells C1 and C2 are good in the example of FIG. 8, when a plurality of other wells 41 which is short of only one good cell C are present, it is possible to cause the first and second tips 12-1 and 12-2 to access these wells 41 and add the cells C1 and C2 to each tip. Examples 1 and 2 are also applicable to a case where a plurality of cells to be removed are present in the partial cell removal in the above Operation 2 (Step S8).

Example 3

FIGS. 9A to 9E are views showing Example 3 of cell handling. Example 3 is mainly applied to the partial cell removal in the above Operation 2 (Step S8). It is assumed, as shown in FIG. 9A, that two cells C1 and C2 are stored in one well 41 as a modification target, of which the cell C2 (a part of the plurality of cells) is selected as a picking target. In this case, the determination unit 75 determines whether or not the two cells C1 and C2 are arranged at a predetermined distance from each other based on arrangement position information about a position, in the well 41, of the cells C1 and C2 specified by the image processing by the image processing unit 74.

Here, the predetermined distance represents a distance at which no cells around a picking target cell are suctioned by the tip 12 when the distal end opening portion t of the tip 12 is caused to approach the picking target cell and when suction force is generated. It is assumed, in the example in FIG. 9A, that the determination unit 75 determines that a distance d1 of the cell C1 to the cell C2 as a picking target satisfies the predetermined distance. In this case, the main control unit 77 causes the distal end opening portion t of the tip 12 to be aligned with the cell C2 in the well 41 to suction the cell C2 (picking of a part of cells/individual suction operation) as shown in FIG. 9B.

In a case where the cell C2 is determined to be a cell (unnecessary cell) not satisfying the determination criterion by the determination unit 75, the main control unit 77 causes the tip 12 (the head main body 62) holding the cell C2 to move to a collection container 42 for collecting (discarding) unnecessary cells and discharge the cell C2 to the collection container 42 as shown in FIG. 9C. Meanwhile, the main control unit 77 causes another tip 12 holding a cell C3 satisfying the determination criterion to access to the well 41 from which the cell C2 has been removed and to discharge the cell C3 to the well 41 as shown in FIG. 9D. The operation in FIG. 9D corresponds to the above Operation 3 (Step S10).

In a case where the cell C2 is a cell (necessary cell) determined to satisfy the determination criterion by the determination unit 75 and the cell C1 is the unnecessary cell, the operation step in FIG. 9B becomes operation of selectively picking a necessary cell. In this case, the collection container 42 shown in FIG. 9C is replaced by a container which collects necessary cells and the operation in FIG. 9D will not be executed. Instead of collecting the cell C2 by the collection container 42, the cell C2 may be discharged to another well 41 having a shortage of the number of cells (see Example 4 to be described next).

On the other hand, FIG. 9E illustrates a case where two cells C1 and C2 are present close to each other in the well 41 and the determination unit 75 determines that a distance d2 of the cell C1 to the picking target cell C2 does not satisfy the predetermined distance. In such a case where the cells C1 and C2 are close to each other as shown above, it is difficult to selectively suction only the cell C2 by the tip 12. In this case, the main control unit 77, for example, causes the tip 12 to suction the cells C1 and C2 by one suction operation and to also discharge the cells to the collection container 42 for discarding. Alternatively, the main control unit 77 may cause suction force and discharge force to be alternately generated at the distal end opening portion t to stir the culture medium in the well 41.

According to Example 3, in a case where the plurality of cells C are arranged at a predetermined distance from each other in the well 41, a part of the cells C is individually picked. This arrangement enables, for example, only unnecessary cells to be picked while enabling necessary cells to remain in the well 41. Such a well 41 only needs addition of an insufficient number of cells C and therefore, the number of cells C required in one well 41 can be efficiently prepared. It is also possible to conduct cell handling in which necessary cells are picked and used for other purposes.

Example 4

Figure 10A:
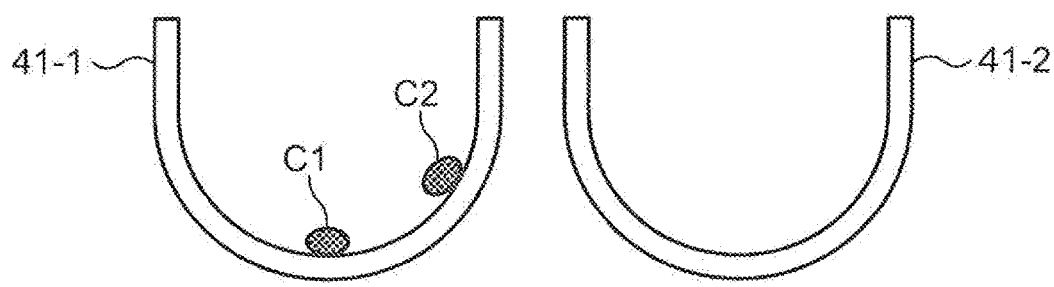
FIGS. 10A to 10C are views showing one example of the cell handling operation.
Figure 10B:
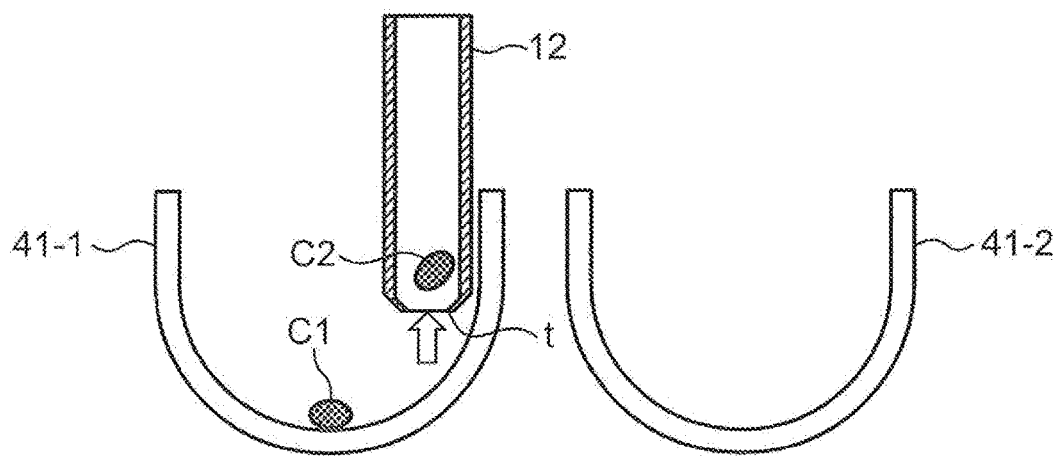
Figure 10C:
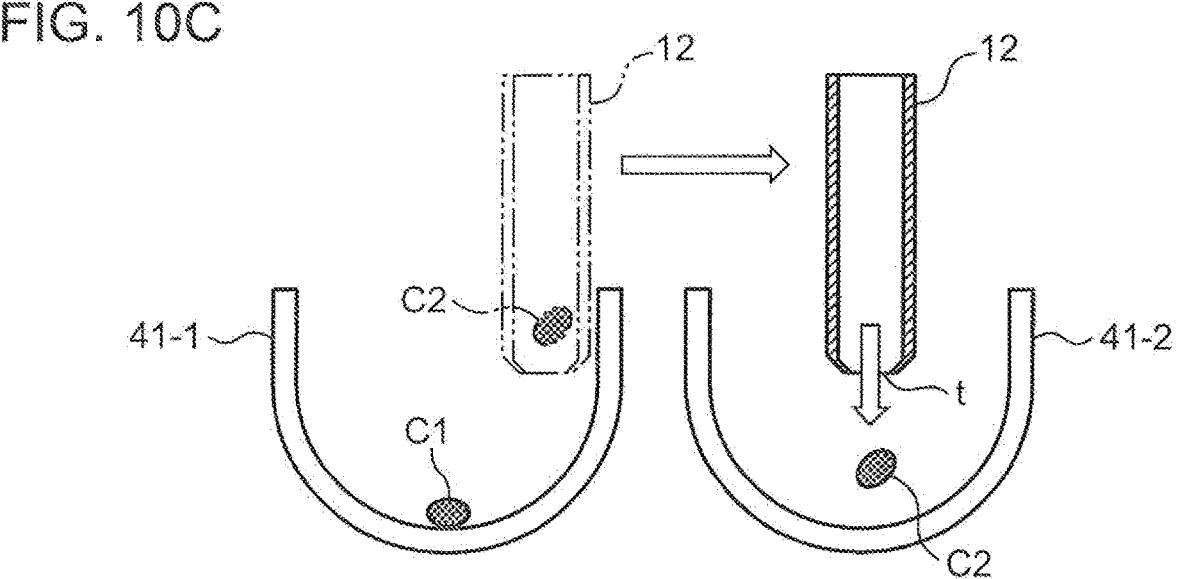

FIGS. 10A to 10C are views showing Example 4 of cell handling. Example 4 shows a specific example of cell addition in the above Operation 3 (Step S10). It is assumed, as shown in FIG. 10A, that two cells C1 and C2 are stored in a first well 41-1 (section). On the other hand, it is assumed that no cell C is stored in a second well 41-2 (another section) other than the first well 41-1. In other words, the second well 41-2 is a well to which the cell C is to be added. Then, it is assumed that both of the cells C1 and C2 are determined to be necessary cells which satisfy the determination criterion by the determination unit 75.

In this case, the main control unit 77 causes the distal end opening portion t of the tip 12 to be aligned with the cell C2 in the first well 41-1 to suction the cell C2 as shown in FIG. 10B. The cell C1 may be suctioned. However, since the cell C1 is positioned near the center of a bottom surface of the first well 41-1 and is therefore suitable for subsequent observation, culture, and the like, it is desirable to pick the cell C2 positioned near an edge of the bottom surface.

Subsequently, the main control unit 77 causes the tip 12 holding the cell C2 to move from the first well 41-1 to the second well 41-2 by moving the head main body 62 as shown in FIG. 10C. Then, the main control unit 77 causes the cell C2 to be discharged from the tip 12 to the second well 41-2. According to such Example 4, the cell C2 picked from the first well 41-1 can be transferred to the second well 41-2 in short of the number of the cells C satisfying the determination criterion. Accordingly, the number of cells C required in one well 41 can be efficiently prepared.

Example 5

Figure 11:
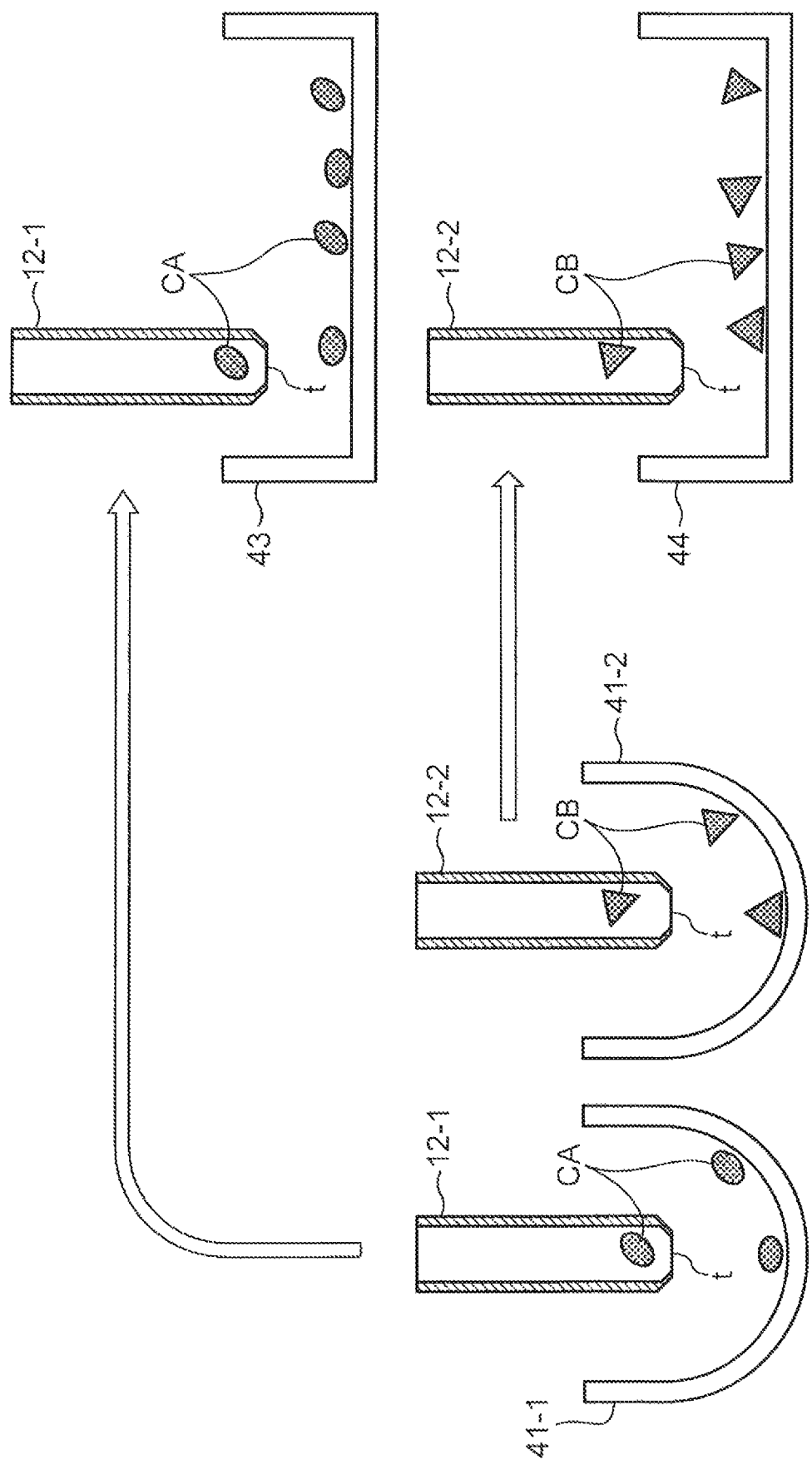
FIG. 11 is a view showing one example of the cell handling operation.

FIG. 11 is a view showing Example 5 of cell handling. Example 5 shows an example in which the cell C picked from the well 41 is transferred to another section divided according to properties of the cell C. It is assumed that a cell CA having a first property is stored in the first well 41-1 (section) and a cell CB having a second property different from the first property is stored in another second well 41-2 (section). The cells CA and CB are cells, for example, which are different from each other in cell type, size, and growth state. As a matter of course, the cells CA and CB can be stored being mixed in the first and second wells 41-1 and 41-2.

In Example 5, a first collection container 43 (another section) and a second collection container 44 (another section) which are divided according to properties of the cell C are prepared. The first collection container 43 is a container for collecting the cell CA and the second collection container 44 is a container for collecting the cell CB.

At the time of collecting the cell CA constituted by a necessary cell or an unnecessary cell, the main control unit 77 causes the distal end opening portion t of the first tip 12-1 to access into the first well 41-1 to suction the cell CA. Subsequently, the main control unit 77 causes the first tip 12-1 holding the cell CA to move from the first well 41-1 to the first collection container 43 by moving the head main body 62, to discharge the cell CA. Similarly, at the time of collecting the cell CB constituted by a necessary cell or an unnecessary cell, the main control unit 77 causes the distal end opening portion t of the second tip 12-2 to access into the second well 41-2 to suction the cell CB. Subsequently, the main control unit 77 causes the second tip 12-2 holding the cell CB to move from the second well 41-2 to the second collection container 44 by moving the head main body 62, to discharge the cell CB.

According to Example 5, the cells CA and CB of different properties which are picked from the first and second wells 41-1 and 41-2 are transferred to the first and second collection containers 43 and 44 prepared according to the properties of the cells C. Accordingly, the cells CA and CB of different properties will not be kept mixed with each other, which is advantageous when the cells CA and CB are reused. Although the first and second collection containers 43 and 44 may be containers prepared separately from the microplate 4, a plurality of other wells 41 provided in the microplate 4 may be replaced by the first and second collection containers 43 and 44, respectively.

Example 6

FIGS. 12A and 12B are views showing Example 6 of cell handling. Example 6 shows an example in which the cell C is returned to a container as a transfer source, the cell C having been transferred from the container as a transfer source to the well 41 which is a container as a transfer destination and picked from the well 41. Example 6 shows a cell holder 23 as a transfer source container of the cell C. The cell holder 23 may be a petri dish or a tube which accumulates the cells C together with a culture medium or may be the dish 2 (the selection container 11) shown above.

As illustrated in FIG. 12A, after the cell C is suctioned from the cell holder 23 by the tip 12, and the tip 12 holding the cell C is moved to the well 41, the cell C is discharged to the well 41. Such a transfer device that conducts cell transfer from the cell holder 23 to the well 41 may be a transfer device prepared separately from the head unit 6 or may be implemented by the head unit 6 (the head device).

After the cell C is transferred to the well 41, the camera unit 5 conducts imaging of the well 41 and also the determination unit 75 executes state determination as to whether or not the cell C satisfies a predetermined determination criterion. The main control unit 77 causes picking of the cell C from the well 41 according to the state determination result of the cell C. For example, when determination is made that the cell C does not satisfy the determination criterion, the main control unit 77 causes execution of operation of returning the cell C to the cell holder 23. Specifically, the main control unit 77 causes the tip 12 to suction the cell C from the well 41 and the tip 12 holding the cell C to move to the cell holder 23 as shown in FIG. 12B. Then, the cell C is discharged from the tip 12 to the cell holder 23.

According to Example 6, the cell C which has been once transferred from the cell holder 23 to the well 41 and is determined not to satisfy the determination criterion in the well 41 is returned to the cell holder 23. It is accordingly unnecessary to prepare a place for keeping or a place for discarding the cell C not satisfying the determination criterion.

Example 7

FIGS. 13A and 13B are views showing Example 7 of cell handling. Example 7 shows an example in which the cell C transferred from the dish 2 to the well 41 and picked from the well 41 is returned to the dish 2.

As illustrated in FIG. 13A, the cell C is held in the holding recess 3 of the dish 2 as a transfer source of the cell C. Some of the holding recesses 3 are empty holding recesses where cells C are not held. It is assumed here that two cells C1 and C2 are stored in a first holding recess 3-1 and the two cells C1 and C2 are transferred to the well 41. The second holding recess 3-2 adjacent to the first holding recess 3-1 is an empty holding recess.

Here, when there occurs a need of picking the cells C1 and C2 from the well 41, for example, when it is found that the number of cells satisfying the determination criterion is in excess in the well 41, the cells C1 and C2 are returned to the dish 2 as a transfer source container similarly to Example 6 above. At this time, the main control unit 77 does not return both of the two cells C1 and C2 to the first holding recess 3-1 where the two cells are originally held, but uses the empty second holding recess 3-2 as shown in FIG. 13B. In other words, the cell C1 is returned to the first holding recess 3-1, and the cell C2 is returned to the second holding recess 3-2.

According to Example 7, the cells C which have been once transferred from the dish 2 to the well 41 and thereafter returned to the dish 2 are again held in order in the holding recess 3. In other words, the cells C1 and C2 can be held one each in the first and second holding recesses 3-1 and 3-2, respectively. Accordingly, at the time of subsequent transfer of the cell C from the dish 2, the head unit 6 is allowed to execute transfer work efficiently with ease.

Example 8

FIGS. 14A to FIG. 15C are views showing Example 8 of cell handling. Example 8 shows an example of reset operation of the well 41 using a large tip 12C. Reset here represents bringing about a state where a new cell C can be accepted by removing all the cells C from the well 41 to which the cells C have been once transferred.

FIG. 14A is a sectional view showing a structure of the large tip 12C. The large tip 12C includes a syringe 13 internally provided with a tubular passage 13H serving as a suction route of the cell C, and a plunger 14 which reciprocates in the tubular passage 13H while being in sliding contact with an inner circumferential wall of the syringe 13. The syringe 13 includes a syringe base end portion 131 configured by a large-diameter cylindrical body, a syringe main body 132 configured by an elongated small-diameter cylindrical body, and a tapered cylinder portion 133 which connects the base end portion 131 and the main body 132 to each other. The tubular passage 13H is formed in the syringe main body 132. The above distal end opening portion t is provided at a distal end of the syringe main body 132. The plunger 14 includes a plunger base end portion 141 configured by a cylindrical body, a columnar plunger main body 142, and a tapered portion 143 which connects the base end portion 141 and the main body 142. In a state where the plunger 14 is inserted most deeply into the syringe 13, a distal end portion 144 of the plunger 14 slightly protrudes from the distal end opening portion t.

The plunger 14 is installed in the syringe 13 such that the plunger main body 142 slides in the tubular passage 13H of the syringe main body 132 in the up-down direction. Upward movement of the plunger 14 with respect to the syringe 13 generates suction force at the distal end opening portion t. On the other hand, downward movement of the plunger 14 generates discharge force at the distal end opening portion t. These suction force and discharge force enable suction of the cell C from the distal end opening portion t and discharge of the suctioned cell C from the distal end opening portion t.

It is assumed that a plurality of cells C are stored in the well 41 together with the culture medium L as shown in FIG. 14B. Then, based on the state determination result made by the determination unit 75, it is assumed that determination is made that none of the cells C satisfies the predetermined determination criterion and should be therefore discarded. In this case, the main control unit 77 executes such operation of resetting the well 41 using the above large tip 12C as shown in FIGS. 14C to FIG. 15C (all cell removal of the above Operation 1). The tubular passage 13H of the large tip 12C has a capacity enabling suctioning of the entire culture medium L filled in the well 41.

As shown in FIG. 14C, prior to the suction of the cell C, the main control unit 77 moves the plunger 14 up and down by a predetermined stroke. As a result, suction force and discharge force are alternately generated at the distal end opening portion t to cause the cells C settled at a bottom portion of the well 41 to rise upward due to a flow of the culture medium L. This facilitates suction of the cell C into the large tip 12C. Then, the main control unit 77 causes the plunger 14 to rise to suction the cell C into the tubular passage 13H together with the surrounding culture medium L (liquid) as shown in FIG. 14D. This suction brings the well 41 into an empty state where neither the cell C nor the culture medium L is present.

Subsequently, the main control unit 77 moves the large tip 12C holding the cell C to a discarding place for the cell C. Example 8 shows an example in which the discarding place is the selection container 11 as shown in FIG. 15A (the selection container 11 is shown to be considerably reduced in size for facilitating the illustration). The main control unit 77 causes the distal end opening portion t of the large tip 12C to enter the upper opening 11H so as to be immersed in the culture medium L accumulated in the selection container 11. Then, the plunger 14 is lowered to discharge the cell C held in the tubular passage 13H to the selection container 11 together with the culture medium L. The discharged cell C is held on the dish 2.

Thereafter, the main control unit 77 causes the plunger 14 to be raised while having the distal end opening portion t being immersed in the culture medium L as shown in FIG. 15B. In this manner, the culture medium L is suctioned into the tubular passage 13H of the large tip 12C. Then, the main control unit 77 causes the large tip 12C holding the culture medium L to a position of the well 41 considered to be empty earlier. Subsequently, the culture medium L is discharged from the large tip 12C to the well 41 as shown in FIG. 15C. As a result, the well 41 is brought into a state for accepting a new cell C.

Example 9

FIGS. 16A to FIG. 17C are views showing Example 9 of cell handling. Example 9 shows an example of operation of picking the cell C from the well 41 and operation of adding the cell C to the well 41 using a small tip 12D.

FIG. 16A is a sectional view showing a structure of the small tip 12D. The small tip 12D includes a small-diameter syringe 15 internally provided with a tubular passage 15H serving as a suction route of the cell C, and a plunger 16 which reciprocates in the tubular passage 15H while being sliding contact with an inner circumferential wall of the syringe 15. The syringe 15 includes a syringe base end portion 151 configured by a large-diameter cylindrical body, a syringe main body 152 configured by an elongated small-diameter cylindrical body, and a tapered cylinder portion 153 which connects the base end portion 151 and the main body 152 to each other. The tubular passage 15H is formed in the syringe main body 152. The above distal end opening portion t is provided at a distal end of the syringe main body 152. The plunger 16 includes a plunger base end portion 161 configured by a cylindrical body, a needle-like plunger main body 162, and a tapered portion 163 which connects the base end portion 161 and the main body 162. In a state where the plunger 16 is inserted most deeply into the syringe 15, a distal end portion 164 of the plunger 16 slightly protrudes from the distal end opening portion t.

The plunger 16 is installed in the syringe 15 such that the plunger main body 162 slides in the tubular passage 15H of the syringe main body 152 in the up-down direction. Upward movement of the plunger 16 with respect to the syringe 15 generates suction force at the distal end opening portion t. On the other hand, downward movement of the plunger 16 generates discharge force at the distal end opening portion t. These suction force and discharge force enable suction of the cell C from the distal end opening portion t and discharge of the suctioned cell C from the distal end opening portion t.

It is assumed that the plurality of cells C are stored in the well 41 together with the culture medium L as shown in FIG. 16B and that determination is made that a part or all of the cells C are cells to be discarded. In this case, the main control unit 77 executes the cell C picking and addition operation (the all cell removal of the above Operation 1 or partial cell removal of the Operation 2) using the above small tip 12D as shown in FIG. 16C to FIG. 17C. The tubular passage 15H of the small tip 12D has a capacity enabling suction of only a part of the culture medium L filled in the well 41.

The main control unit 77 causes the small tip 12D to enter the well 41 to make the distal end opening portion t close to the cell C in the culture medium L as shown in FIG. 16C. Then, the plunger 16 is raised to allow the cell C to be suctioned into the tubular passage 15H together with the surrounding culture medium L. The suction brings the well 41 into a state where only the culture medium L is present without the cell C, or a state where only the necessary cells C remain together with the culture medium L.

Subsequently, the main control unit 77 moves the small tip 12D holding the cell C to the selection container 11 as a discarding place of the cell C as shown in FIG. 17A. Subsequently, the main control unit 77 causes the distal end opening portion t of the small tip 12D to enter the upper opening 11H so as to be immersed in the culture medium L accumulated in the selection container 11. At this time, the alignment may be made with a specific holding recess 3. Then, the plunger 16 is lowered to discharge the cell C held in the tubular passage 15H to the selection container 11 together with the culture medium L. The discharged cell C is held on the dish 2.

Thereafter, the main control unit 77 causes the distal end opening portion t of the small tip 12D to be aligned with a cell CT carried at a place other than a discarding region of the dish 2 and satisfying the determination criterion as shown in FIG. 17B. Then, the plunger 16 is raised to suction the cell CT together with the culture medium L. Thereafter, the main control unit 77 causes the small tip 12D holding the cell C to be moved to a position of the well 41 from which the cell C has been picked earlier. Subsequently, the small tip 12D is caused to discharge the cell CT together with the culture medium L to the well 41 as shown in FIG. 17C. This brings about a state where the cell CT is added to the well 41.

Other Embodiments

Although various embodiments of the present disclosure have been described in the foregoing, the present disclosure is not limited thereto and can further assume other embodiments shown below.

(1) In the above embodiments, the camera unit 5 is illustrated as one example of the cell detection unit for cells stored in the well 41. In other words, an example of detecting the cell C based on an image is illustrated. The cell detection unit may be a physical quantity sensor such as an optical or audio sensor. For example, the cell C may be illuminated with a beam to observe its fluorescence, thereby recognizing the cell C. Alternatively, using a sonar having a sound source, the cell C may be recognized based on an echoing sound.

(2) In the above embodiments, the microplate 4 having the well 41 is mainly illustrated as a container having a section capable of storing cells. In another possible mode, with the dish 2 as the container and the holding recess 3 as the section, picking and release of the cell C, and addition of the cell C may be conducted with respect to the holding recess 3.

(3) In the above embodiments, the head unit 6 with the tip 12 is illustrated as an example of the head device, suction of the cell C to the tip 12 is illustrated as a mode of picking, and discharge of the suctioned cell C from the tip 12 is illustrated as a mode of release. These are examples only and any head device can be used as long as it can hold one or a plurality of cells C by mechanical, electrical, magnetical force, or the like and release the held cells C.

The above-described specific embodiments mainly include the disclosure having the following components.

A cell handling device according to one aspect of the present disclosure includes a container having a section capable of storing cells; a cell detection unit which detects a cell stored in the section; a head device which conducts picking of cells, and transfer and release of the picked cells; a control unit which controls operation of the head device; and a determination unit which makes a determination of a cell state including at least one of the number, properties and arrangement of the cells stored in the section based on a detection result of the cell detection unit. The control unit causes the head device to execute, according to a state determination result obtained by the determination unit, one operation selected from among operation of picking all the cells stored in the section, operation of picking a part of the cells stored in the section, operation of picking a new cell and releasing the cell in the section, and operation of terminating processing of the section.

According to the cell handling device, any one of the following operations is selected based on a state of a cell determination result: for example, the operation of picking all or a part of cells in a case where a cell in an inappropriate state is stored in the section, the operation of adding a new cell to the section in a case of a shortage of a cell, and the operation of terminating processing of the section in which a cell is stored as intended. Accordingly, it is possible to modify a state of the container in which a cell has been once stored in the section to a state where cells are stored as intended by the cell handling device.

In the above cell handling device, it is preferable that state determination by the determination unit is for determining whether or not a cell as a determination target satisfies a determination criterion set in advance regarding the properties, and the control unit causes the head device to execute operation of picking all cells determined not to satisfy the determination criterion from the section.

According to the cell handling device, a cell not satisfying the determination criterion is removed from the section to bring the section into a so-called reset state. Accordingly, it is possible to modify the state to be a state where the cells are stored in the section as intended by again inserting a cell which satisfies the determination criterion to the section.

In the above cell handling device, in the state determination, when the determination unit determines that a plurality of cells are present in the section and the cells are arranged at a predetermined distance from each other, the control unit preferably causes the head device to execute operation of picking a part of the plurality of cells.

In a case where a plurality of cells are arranged at a predetermined distance from each other in the section, the cells can be individually picked with ease. This cell handling device enables, for example, only cells in a defective state to be picked up while enabling cells in a good state to remain in the section. Such a section only needs addition of an insufficient number of cells and therefore, the number of cells required in one section can be efficiently prepared. The above cell handling device also enables cell handling in which cells in a good state are picked and used for other purposes.

In the above cell handling device, it is preferable that the container has another section in addition to the section, and the control unit causes the head device to execute operation of transferring and releasing a cell picked from the section to the other section.

According to the cell handling device, a cell picked from the section can be transferred to another section in short of the number of cells in a good state. Accordingly, the number of cells required in one section can be efficiently prepared.

In the above cell handling device, it is preferable that another section which is a cell storage and is divided according to properties of a cell is further provided and the control unit causes the head device to execute operation of transferring and releasing a cell picked from the section to the other section.

According to the cell handling device, the picked cells are transferred to another section divided according to the properties of the cells. Accordingly, the cells of different properties will not be kept mixed with each other, which is advantageous when the cells are reused. The other section may be another section provided in the container or may be another container.

The above cell handling device preferably further includes a cell holder which holds a cell to be stored in the section of the container; and a transfer device which transfers a cell from the cell holder to the section of the container, in which the determination unit conducts the state determination with respect to a cell transferred from the cell holder to the section.

According to the cell handling device, state determination is made of a cell transferred from the cell holder to the section of the container by the transfer device. Specifically, with the cell holder as a cell transfer source and the container as a cell transfer destination, state determination of a cell is made at the transfer destination. Accordingly, it is possible to apply the cell handling device of the present disclosure to a common cell transfer device to form a state where cells are stored as intended in the section of the container as the transfer destination.

In the above cell handling device, it is preferable that the determination unit executes state determination for determining whether or not a cell transferred from the cell holder to the section satisfies the determination criterion set in advance regarding properties, and the control unit causes the head device to execute operation of picking the cell from the section and returning the cell to the cell holder according to the state determination result.

According to the cell handling device, a cell which has been once transferred to the section but is determined, for example, not to satisfy the determination criterion is returned to the cell holder. Accordingly, a place for keeping or a place for discarding a cell not satisfying the determination criterion is unnecessary.

In the above cell handling device, it is preferable that the cell holder includes a plurality of holding portions independently holding one or a plurality of cells, and the control unit causes the head device to execute, in the operation of returning the picked cell to the cell holder, operation of returning the cell to an empty holding portion among the plurality of holding portions.

According to the cell handling device, cells which have been once transferred from the cell holder to the section and thereafter returned to the cell holder are again held in order in the holding portion of the cell holder. Accordingly, at the time of subsequent transfer of the cell from the cell holder, the transfer device is allowed to execute transfer work efficiently with ease.

In the above cell handling device, the head device preferably also serves as the transfer device. This simplifies a configuration of the cell handling device.

In the above cell handling device, it is preferable that in the section, cells are dispersed in liquid, and the head device includes a tip having a distal end opening portion allowing suction of a cell and discharge of the suctioned cell, the tip suctioning the cell together with surrounding liquid during the picking, and discharging the cell together with the suctioned liquid during the release.

According to the cell handling device, suction and discharge by the tip enables picking and release of a cell to realize simplification and facilitation of these works.

In this case, it is preferable that in a case of picking a plurality of cells from the section, the control unit causes the head device to execute, when a distance between the plurality of cells is shorter than a predetermined distance, operation of causing the tip to suction the plurality of cells by one suction operation, and when the distance between the plurality of cells is longer than the predetermined distance, operation of causing the tip to suction each of the plurality of cells by individual suction operation.

The cell handling device allows the tip to execute suction operation according to an arrangement mode of cells in the section. Specifically, in a case where a plurality of cells are arranged close to each other in the section, it is difficult to individually suction these cells by the tip. In this case, the tip is caused to suction the plurality of cells by one suction operation. By contrast, in a case where a plurality of cells are spaced apart from each other in the section, these cells can be individually suctioned by the tip. Accordingly, in this case, the tip is caused to suction each cell by individual suction operation.

It is preferable that the above cell handling device further includes another head device in addition to the head device, in which when causing picking of a plurality of cells from the section, the control unit selects whether to cause any one of the head device and the other head device to pick the plurality of cells, or to cause the head device and the other head device to share picking of the plurality of cells.

According to the cell handling device, by making use of the head device and the other head device, picking patterns of the cells can be diversified.

In the above cell handling device, the cell detection unit preferably includes an imaging device which obtains an image of a cell stored in the section.

According to the cell handling device, by subjecting an image obtained by the imaging device to image processing, or the like, cells stored in the section can be reliably detected with ease.

According to the present disclosure described above, a cell handling device can be provided which is capable of bringing a container having a section for storing cells into a state where cells are stored as intended.

What is claimed is:

1. A cell handling device comprising:
   a container having wells as a section configured to store cells;
   a cell detector configured to detect a cell stored in the section;
   head devices configured to conduct picking of cells, and transfer and release of the picked cells; and
   a controller configured to control operation of the head devices; wherein
   the controller is configured to make a determination of a cell state including at least one of the number, properties and arrangement of the cells stored in the section based on a detection result of the cell state,
   wherein the controller is configured to cause the head device to execute, according to a state determination result obtained by the determination unit, one operation selected from among
   operation of picking all the cells stored in the section,
   operation of picking a part of the cells stored in the section,
   operation of picking a new cell and releasing the cell in the section,
   operation of terminating processing of the section, and wherein
   the head devices include a first head device and a second head device each capable of carrying out the operation of picking and releasing the cell to a specific well of the wells,
   the state determination by the controller is for determining whether or not a cell as a determination target satisfies a determination criterion set in advance regarding the properties,
   the controller is configured to cause the head device to execute operation of picking all cells determined not to satisfy the determination criterion from the section, and
   when causing picking of a plurality of cells from the specific well, the controller is configured to select whether to
   cause any one of the first head device and the second head device to pick the plurality of cells, or
   cause the first head device and the second head device to share picking of the plurality of cells, and
   determine release patterns of the picked cells.

2. The cell handling device according to claim 1, wherein the container has another section in addition to the section, and
   the controller is configured to cause the head device to execute operation of transferring and releasing a cell picked from the section to the other section.

3. The cell handling device according to claim 1, further comprising:
   another section which is a cell storage and is divided according to properties of a cell,
   wherein the controller is configured to cause the head device to execute operation of transferring and releasing a cell picked from the section to the other section.

4. The cell handling device according to claim 1, further comprising:
   a cell holder configured to hold a cell to be stored in the section of the container; and
   a transfer device configured to transfer a cell from the cell holder to the section of the container,
   wherein the controller is configured to conduct the state determination with respect to a cell transferred from the cell holder to the section.

5. The cell handling device according to claim 4, wherein
   the controller is configured to execute state determination for determining whether or not a cell transferred from the cell holder to the section satisfies the determination criterion set in advance regarding properties, and
   the controller is configured to cause the head device to execute operation of picking the cell from the section and returning the cell to the cell holder according to the state determination result.

6. The cell handling device according to claim 5, wherein
   the cell holder includes a plurality of holding portions configured to independently hold one or a plurality of cells, and
   the controller is configured to cause the head device to execute, in the operation of returning the picked cell to the cell holder, operation of returning the cell to an empty holding portion among the plurality of holding portions.

7. The cell handling device according to claim 4, wherein the head device also serves as the transfer device.

8. The cell handling device according to claim 1, wherein
   in the section, cells are dispersed in liquid, and
   the head device includes a tip having a distal end opening portion allowing suction of a cell and discharge of the suctioned cell,
   the tip suctioning the cell together with surrounding liquid during the picking, and discharging the cell together with the suctioned liquid during the release.

9. The cell handling device according to claim 8, wherein
   in a case of picking a plurality of cells from the section, the controller is configured to cause the head device to execute:
   when a distance between the plurality of cells is shorter than a predetermined distance, operation of causing the tip to suction the plurality of cells by one suction operation, and
   when the distance between the plurality of cells is longer than the predetermined distance, operation of causing the tip to suction each of the plurality of cells by individual suction operation.

10. The cell handling device according to claim 1, wherein
    the cell detector includes an imaging device configured to obtain an image of a cell stored in the section.

* * * * *